(12) United States Patent
Fernandes et al.

(10) Patent No.: US 8,590,573 B2
(45) Date of Patent: Nov. 26, 2013

(54) MICROFABRICATED FLUIDIC CIRCUIT ELEMENTS AND APPLICATIONS

(75) Inventors: David Fernandes, Pacifica, CA (US); Hou-Pu Chou, Sunnyvale, CA (US); Marc A. Unger, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 13/337,866

(22) Filed: Dec. 27, 2011

(65) Prior Publication Data

US 2013/0000765 A1 Jan. 3, 2013

Related U.S. Application Data

(60) Division of application No. 12/621,108, filed on Nov. 18, 2009, now Pat. No. 8,104,514, which is a continuation of application No. 12/144,603, filed on Jun. 23, 2008, now Pat. No. 7,640,947, which is a continuation of application No. 11/213,598, filed on Aug. 26, 2005, now Pat. No. 7,392,827, which is a continuation of application No. 10/927,688, filed on Aug. 27, 2004, now Pat. No. 6,953,058, which is a division of application No. 09/995,397, filed on Nov. 26, 2001, now Pat. No. 6,802,342.

(60) Provisional application No. 60/282,253, filed on Apr. 6, 2001.

(51) Int. Cl.
*F16K 15/16* (2006.01)

(52) U.S. Cl.
USPC .......................................... 137/829; 137/855

(58) Field of Classification Search
USPC .......... 137/825, 829, 832, 843, 852, 855, 856
See application file for complete search history.

(56) References Cited

U.S. PATENT DOCUMENTS

| | | |
|---|---|---|
| 3,199,781 A | 8/1965 | Welsh |
| 3,359,863 A | 12/1967 | Phillips |
| 3,503,423 A | 3/1970 | Edell |
| 3,643,861 A | 2/1972 | Eckerlin |
| 3,650,181 A | 3/1972 | Parr |
| 3,747,628 A | 7/1973 | Holster et al. |

(Continued)

FOREIGN PATENT DOCUMENTS

| | | |
|---|---|---|
| DE | 044 22 943 | 1/1996 |
| DE | 198 16 283 | 10/1999 |

(Continued)

OTHER PUBLICATIONS

Foster et al., "Fluidics Components and Circuits", Wiley-Interscience, 1970.

(Continued)

*Primary Examiner* — Craig Schneider
(74) *Attorney, Agent, or Firm* — Kilpatrick Townsend & Stockton LLP

(57) ABSTRACT

A microfabricated fluidic unidirectional valve includes a microfabricated elastomer material having a flow through channel. The microfabricated fluidic unidirectional valve also includes an elastomer flap attached to the elastomer material in the flow through channel. The elastomer flap forms a seal in the flow through channel to prevent fluid from flowing in a first direction through the flow through channel and to allow fluid flow in a second direction through the flow through channel.

10 Claims, 29 Drawing Sheets

(56) References Cited

U.S. PATENT DOCUMENTS

| | | | |
|---|---|---|---|
| 3,768,521 | A | 10/1973 | Brychta et al. |
| 3,918,677 | A | 11/1975 | Cowan |
| 3,986,527 | A | 10/1976 | Mon |
| 4,248,267 | A | 2/1981 | Brandenberg |
| 4,514,742 | A | 4/1985 | Suga et al. |
| 4,585,209 | A | 4/1986 | Aine et al. |
| 4,895,500 | A | 1/1990 | Hok et al. |
| 5,367,878 | A | 11/1994 | Muntz et al. |
| 5,583,281 | A * | 12/1996 | Yu ................................ 73/23.42 |
| 5,642,015 | A | 6/1997 | Whitehead et al. |
| 5,775,371 | A | 7/1998 | Pan et al. |
| 5,789,045 | A | 8/1998 | Wapner et al. |
| 5,899,218 | A * | 5/1999 | Dugan ............................. 137/1 |
| 6,033,191 | A | 3/2000 | Kamper et al. |
| 6,408,878 | B2 | 6/2002 | Unger et al. |
| 6,431,212 | B1 | 8/2002 | Hayenga et al. |
| 6,802,342 | B2 | 10/2004 | Fernandes et al. |
| 6,953,058 | B2 | 10/2005 | Fernandes et al. |
| 7,392,827 | B2 | 7/2008 | Fernandes et al. |
| 7,640,947 | B2 | 1/2010 | Fernandes et al. |
| 8,104,514 | B2 * | 1/2012 | Fernandes et al. ............ 137/829 |

FOREIGN PATENT DOCUMENTS

| | | |
|---|---|---|
| EP | 1 065 378 | 1/2001 |
| FR | 1 057 817 | 3/1954 |
| GB | 1 041 429 | 9/1966 |
| GB | 1 055 045 | 1/1967 |
| GB | 1 278 831 | 6/1972 |
| GB | 1 285 877 | 8/1972 |
| WO | WO 95/08716 | 3/1995 |
| WO | WO 96/28664 | 9/1996 |
| WO | WO 99/65664 A1 | 12/1999 |
| WO | WO 01/01025 A2 | 1/2001 |

OTHER PUBLICATIONS

Groisman et al., "Elastic turbulence in a polymer solution flow", Nature vol. 405, May 4, 2000.

Joyce et al., "Fluidics Basic Components and Applications", Sep. 1979.

Kim et al., "A three-dimensionally silicon-micromachined fluidic amplifier device,", J. Micromech. Microeng., 1998.

Unger et al., "Monolithic Microfabricated Valves and Pumps by Multilayer Soft Lithography", Science vol. 288, Apr. 7, 2000.

\* cited by examiner

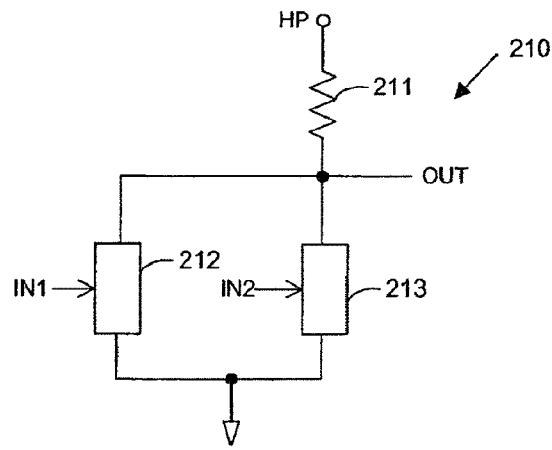
FIG. 12G
FIG. 12H
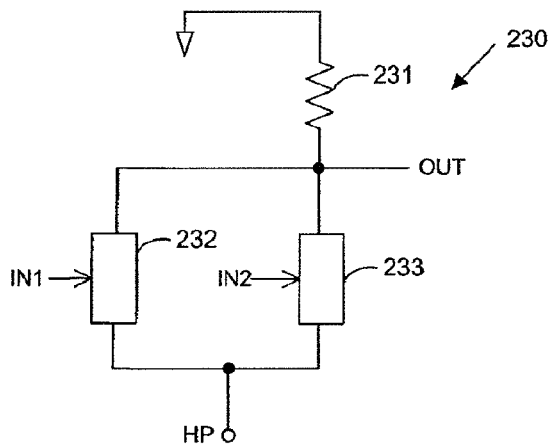
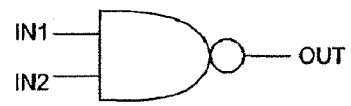
FIG. 12I
FIG. 12J
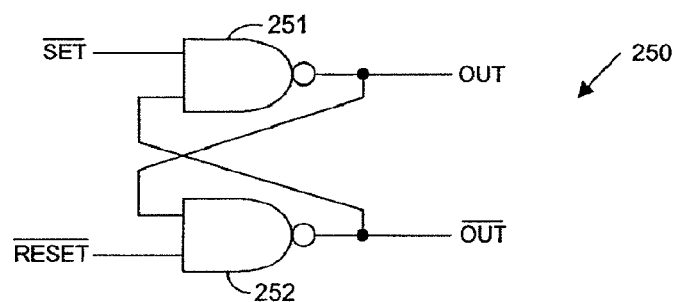
FIG. 13

MICROFABRICATED FLUIDIC CIRCUIT ELEMENTS AND APPLICATIONS

CROSS-REFERENCES TO RELATED APPLICATIONS

This application is a division of Ser. No. 12/621,108, filed Nov. 18, 2009; which is a continuation of U.S. patent application Ser. No. 12/144,603, filed Jun. 23, 2008 (now U.S. Pat. No. 7,640,947); which is a continuation of U.S. patent application Ser. No. 11/213,598, filed Aug. 26, 2005 (now U.S. Pat. No. 7,392,827); which is a continuation of U.S. patent application Ser. No. 10/927,688, filed Aug. 27, 2004 (now U.S. Pat. No. 6,953,058); which is a division of U.S. patent application Ser. No. 09/995,397 (now U.S. Pat. No. 6,802,342), filed Nov. 26, 2001; which claims the benefit of U.S. Provisional Patent Application No. 60/282,253, filed Apr. 6, 2001. The disclosures of these applications are hereby incorporated by reference in their entirety.

BACKGROUND OF THE INVENTION

The present invention relates to microfabricated fluidic systems and methods for regulating the flow of fluid to provide switches, logic gates, latches, pressure sources, analog devices, capacitors, unidirectional valves, pressure multipliers, and devices that perform mathematical functions.

Microfabricated fluidic chips may be used for biological assays. For example, microfabricated fluidic chips may be used to perform biological assays using external control lines that control the opening and closing of on-chip fluidic valves. The on-chip fluidic valves control the flow of fluids in biological assays. The valves are opened and closed using macroscopic pressure sources that are located off-chip, and which are connected through control lines to the chip. In complex assays, a large number of macroscopic control lines is cumbersome and undesirable. Previously known electrical actuating devices have not been able to provide sufficient force by themselves to open or close a fluidic valve.

It would therefore be desirable to provide pressure sources and control lines on-chip that control the opening and closing of on-chip valves so that macroscopic control lines exiting the chip are minimized or eliminated. Previously known on-chip systems have not been adequate to provide control of numerous on-chip valves. Each valve requires a pressure differential between the input and the output to control the valve. Numerous valves coupled together to perform complex functions would require very large pressure differentials to drive all of the cascaded valves. Pressure sources that generate such very high pressure differentials are difficult to manufacture on a microfabricated chip.

Furthermore, such cascaded valve systems do not allow for the introduction of feedback elements. A feedback element is one whereby a (downstream) output pressure, which is controlled by an upstream valve or is controlled by a valve which is controlled by the upstream valve (and so on), in turn controls the function of the upstream valve. The elimination of the possibility of feedback precludes the construction of entire classes of analog devices and digital logic devices (e.g., latches).

It would also be desirable to provide numerous microfabricated fluidic switches on-chip that open and close channels without the need for large pressure differentials.

It would also be desirable to provide devices that perform logic functions, signal latching, mathematical functions, and other complex functions on-chip.

It would also be desirable to provide microfabricated fluidic switches on-chip that incorporate the feed back of information from a downstream part of the circuit to an upstream part.

SUMMARY OF THE INVENTION

It is therefore an object of the present invention to provide pressure sources and control lines that control the opening and closing of valves on-chip so that macroscopic control lines exiting the chip are minimized or eliminated.

It is also an object of the present invention to provide numerous microfabricated fluidic switches on-chip that open and close channels without the need for large pressure differentials.

It is also an object of the present invention to provide devices that perform logic functions, signal latching, mathematical functions, and other complex functions on-chip.

It is also an object of the present invention to provide microfabricated fluidic switches on-chip that incorporate the feed back of information from a downstream part of the circuit to an upstream part.

The present invention sets forth systems and methods for designing and operating microfabricated fluidic (i.e., microfluidic) devices such as switches, logic gates and latches (e.g., flip-flops) that provide control signals which can be fabricated on microfluidic chips. The microfluidic switches, logic gates, and latches of the present invention may operate entirely on-chip without the need for off-chip pressure sources.

The present invention also provides on-chip pressure sources that can drive the microfluidic switches, logic gates and latches. The present invention also provides on-chip microfluidic unidirectional valves, capacitors, switching regulators, and pressure multipliers, that are formed with elastomer material that can also operate without off-chip pressure sources. The devices and methods of the present invention control and channel fluid movement on-chip to perform a variety of functions.

Microfabricated fluidic devices of the present invention may be configured to imitate the functionality of semiconductor circuits, such as ON/OFF switches, capacitors, logic gates, latches, switching regulators, and devices that perform mathematical functions. The microfabricated fluidic logic gates of the present invention include AND gates, OR gates, NOR gates, NAND gates, inverters, and numerous other Boolean and logic functions. The logic functions performed by the microfabricated fluidic devices may also be configured to perform mathematical functions such as addition, subtraction, multiplication, and division.

Microfabricated fluidic (i.e., microfluidic) devices of the present invention may also perform analog functions such as amplification or regulation. For example, devices of the present invention include switching regulators, capacitors, pressure multipliers, and pressure sources. Other analog functions may also be performed using microfluidic devices of the present invention.

BRIEF DESCRIPTION OF THE DRAWINGS

FIG. 12G shows an example of an AND logic gate formed with microfabricated fluidic devices;

FIG. 12H shows the symbol for a two input AND gate;

FIG. 12I shows an example of a NAND logic gate formed with microfabricated fluidic switches;

FIG. 12J shows the symbol for a two input NAND gate;

FIG. 13 is one example of an S-R flip-flop that is constructed with two cross-coupled NAND gates;

DETAILED DESCRIPTION OF THE INVENTION

One embodiment of the present invention includes microfabricated fluidic (i.e., microfluidic) devices that amplify pressure. Pressure may be increased in a first chamber to provide an amplified pressure increase in a second chamber. Microfluidic devices that amplify pressure are referred to as pressure amplifiers or pressure multipliers. In the present application, the term "fluid" may refer to gas or a liquid.

Figure 1:
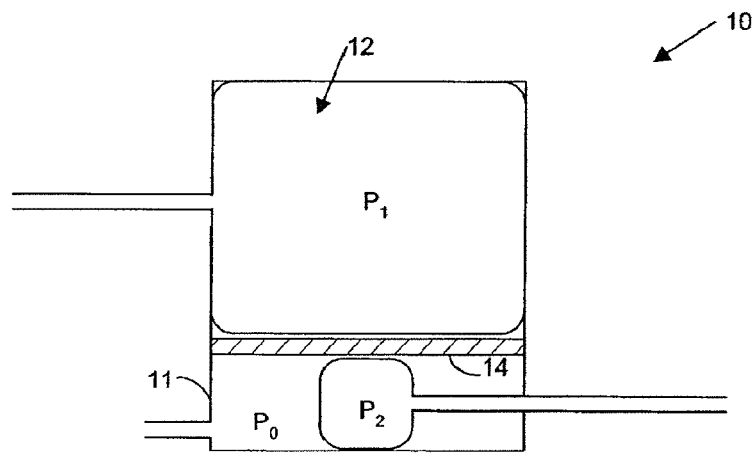
FIG. 1 shows an example of a macroscopic pressure amplification system.

An example of a macroscopic pressure amplification system 10 is shown in FIG. 1. System 10 includes two hollow bladders 12 and 13 which have flexible walls. Bladders 12 and 13 are both inside hollow chamber 11 which comprises rigid, immovable walls. Chamber 11 is filled with a fluid at ambient pressure $P_0$. Bladder 12 is filled with a fluid at a first pressure $P_1$, and bladder 13 is filled with a fluid at a second pressure $P_2$. Bladders 12 and 13 are separated by a rigid material 14. When pressure $P_1$ in bladder 12 is increased sufficiently above pressure $P_0$, bladder 12 expands against material 14, causing rigid material 14 to be pushed against the walls of bladder 13. The volume of bladder 13 decreases, and $P_2$ increases. The pressure $P_2$ in bladder 13 increases above the final value of pressure $P_1$, according to the following simplified equation:

$$\frac{P_2}{P_1} = \frac{A_1}{A_2} \quad (1)$$

where $A_1$ is the surface area of bladder 12 that contacts rigid material 14 when bladder 12 expands against it, and $A_2$ is the surface area of bladder 13 that contacts rigid material 14 when rigid material 14 presses against it.

Bladder 13 must exert a force against rigid material 14 that is equal to the force exerted by bladder 12 against rigid material 14 to achieve a steady state. Because $A_1$ is greater than $A_2$ as can be seen in FIG. 1, pressure $P_2$ increases above $P_1$ when rigid material 14 expands against bladder 13 according to equation (1) to achieve a steady state. System 10 is a pressure amplification system that amplifies pressure $P_2$ with respect to pressure $P_1$.

Pressure changes in pressure $P_1$ and $P_2$ with respect to FIG. 1 may be in the range of 0-1000 psi. Pressure changes in any of the embodiments of the present invention may also be in the range of 0-1000 psi. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, and 1000 psi.

Figure 2:
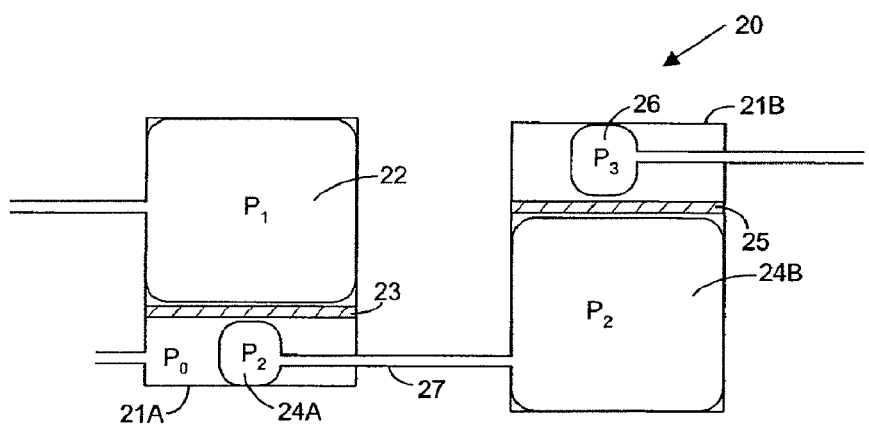
FIG. 2 shows another example of a macroscopic pressure amplification system.

Another example of a macroscopic pressure amplification system 20 is shown in FIG. 2. System 20 includes four hollow bladders 22, 24A, 24B, and 26 which each have flexible walls. Bladders 22 and 24A are inside hollow chamber 21A which comprises rigid, immovable walls. Bladders 24B and 26 are inside hollow chamber 21B which also comprises rigid, immovable walls. Chambers 21A-21B is filled with fluid at ambient pressure $P_0$. Bladder 22 is filled with a fluid at a first pressure $P_1$, bladders 24A and 24B are filled with a at a second pressure $P_2$, and bladder 26 is filled with a fluid at a third pressure $P_3$. Bladders 22 and 24A are separated by a rigid material 23, and bladders 24B and 26 are separated by rigid material 25.

When pressure $P_1$ in bladder 22 is increased above pressure $P_0$, the pressure $P_2$ in bladder 24A increases above the final value of pressure $P_1$ The pressure $P_2$ in bladder 24B is the same as the pressure $P_2$ in bladder 24A, because bladders 24A and 24B are coupled together through channel 27 and both bladders are filled with a fluid. Therefore, pressure $P_2$ in bladder 24B increases by the same amount as pressure $P_2$ in bladder 24A. When pressure $P_2$ in bladders 24A and 24B increases, pressure $P_3$ in bladder 26 increases above the final value of pressure $P_2$. Because the surface area of bladder 24B that contacts rigid material 25 when bladder 24B expands against it is greater than the surface area of bladder 26 that contacts rigid material 25 when rigid material 25 presses against it, as can be seen in FIG. 2, pressure $P_3$ increases above $P_2$ when rigid material 25 expands against bladder 26 to achieve a steady state. System 20 is a pressure amplification system that amplifies pressure $P_2$ with respect to pressure $P_1$ according to equation (1), and amplifies $P_3$ with respect to $P_2$ according to equation (1).

Figure 3:
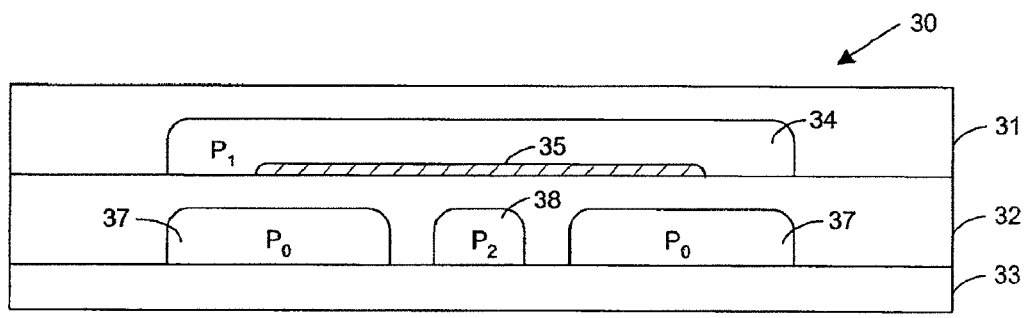
FIGS. 3, 4A, and 4B show a first embodiment of a microfabricated fluidic pressure amplifier (or pressure multiplier) of the present invention.
Figure 4A:
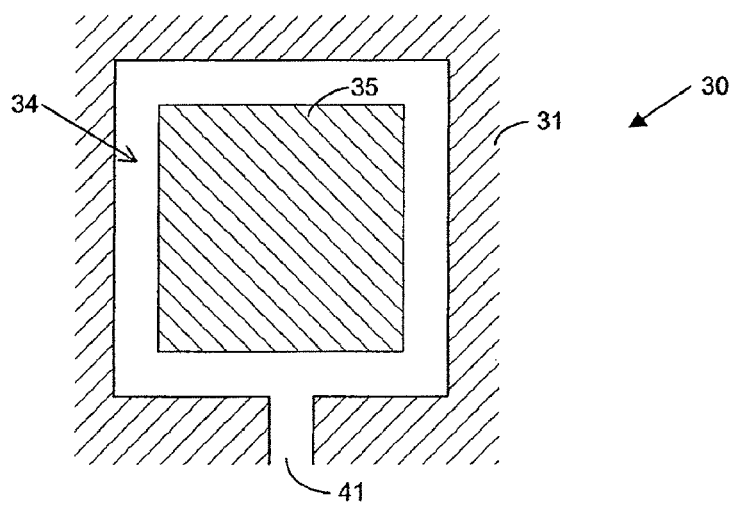
Figure 4B:
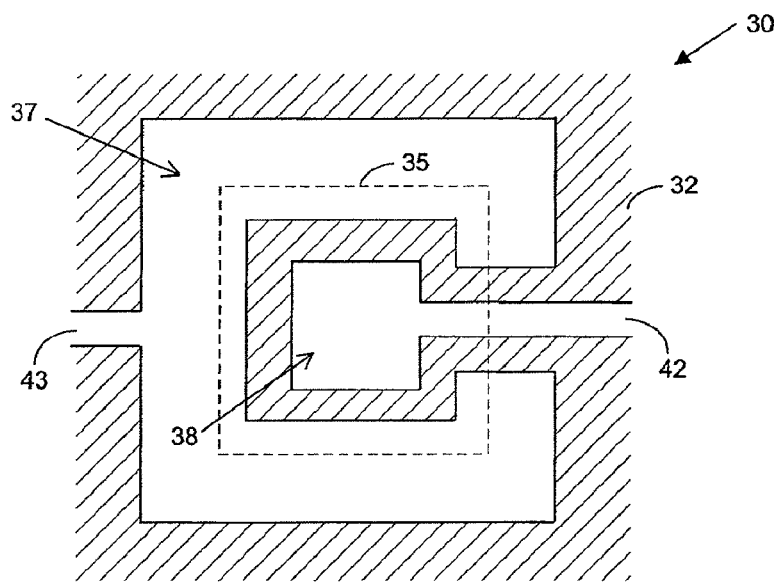

A first embodiment of a microfabricated fluidic pressure amplifier (or pressure multiplier) of the present invention is shown in FIGS. 3, 4A and 4B. Pressure multiplier 30 shown in FIG. 3 is a cross sectional view of a microfabricated fluidic pressure amplifier that contains pre-cured elastomer layers 31 and 32 that are formed on top of rigid planar substrate 33 (e.g., glass). There are many, many types of elastomeric polymers. Common elastomeric polymers that may be used to form elastomer layers 31-32 and other elastomer layers of the present invention include polyisoprene, polybutadiene, polychloroprene, polyisobutylene, poly(styrene-butadiene-styrene), the polyurethanes, and silicones.

Layer 31 has chamber 34, and layer 32 has chambers 37-38. Layers 31-32 and other elastomer layers used to form microfluidic devices of the present invention may be formed and hermetically sealed together using methods discussed in further detail in Microfabricated Elastomeric Valve and Pump Systems, PCT Patent Application Number PCT/US00/17740 filed Jun. 27, 2000 to Unger et al., which designates the United States and is hereby incorporated by reference herein in its entirety.

Layers 31-32 may be, for example, 1-1000 microns thick. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, and 1000 microns.

Chamber 34 may be, for example, 2.5-5000 microns wide. Specific examples include 2.5, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Channel 38 may be, for example, 0.1-250 microns wide. Specific examples include 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, 100, 120, 140, 160, 180, 200, 210, 220, and 225 microns.

Layer 35 may be, for example, 1-100 microns thick. Specific examples include 1, 2, 3, 4, 5, 6, 7, 8, 9, 10, 20, 30, 40, 50, 60, 70, 80, 90, and 100 microns.

In a preferred aspect, the present invention uses a multilayer soft lithography process to build integrated (i.e.: monolithic) microfabricated elastomeric structures. Advantages of fabricating the present structures by binding together layers of soft elastomeric materials include the fact that the resulting devices are reduced by more than two orders of magnitude in size as compared to silicon-based devices. Further advantages of rapid prototyping, ease of fabrication, and biocompatability are also achieved.

In preferred aspects of the invention, separate elastomeric layers such as layers 31-32 are fabricated on top of micromachined molds such that recesses are formed in each of the various elastomeric layers. By bonding or sealing these various elastomeric layers together, the recesses extending along the various elastomeric layers form flow channels and control lines through the resulting monolithic, integral elastomeric structure. In various aspects of the invention, these flow channels and control lines which are formed in the elastomeric structure can be actuated to function as micro-pumps and micro-valves, as will be explained.

A top view of layer 31 is shown in FIG. 4A. Chamber 34 has inlet port 41. Layer 35 comprises a rigid material that can be deposited on elastomer layer 32. Rigid layer 35 and other rigid layers used in microfluidic pressure multipliers and switches of the present invention may comprise material such as polymethomethacrylate (PMMA). Layer 31 is then placed on top of layer 32 so that layer 35 is inside of chamber 34 as shown in FIGS. 3 and 4A. A top view of layer 32 is shown in FIG. 4B. Chamber 37 of layer 32 comprises two branches that surround most of chamber 38. Chamber 37 has inlet port 43, and chamber 38 has inlet port 42.

Chamber 37 is filled with fluid at ambient pressure $P_0$ through inlet port 43. Chamber 34 is filled with a fluid at pressure $P_1$ through port 41, and chamber 38 is filled with a fluid at pressure $P_2$ through port 42. When pressure $P_1$ in chamber 34 is increased above ambient pressure $P_0$, rigid layer 35 expands downward against chambers 37 and 38 causing pressure $P_2$ in chamber 38 to increase above $P_1$. The device of FIGS. 3 and 4A-4B is a pressure multiplier like the devices of FIGS. 1 and 2. Pressure $P_2$ is amplified to a value greater than the final value of $P_1$ when $P_1$ is increased above $P_0$, according to the following equation:

$$P_2 = aP^1 - bP_0 - c \qquad (2)$$

Referring to FIGS. 3, and 4A-4B, a is the ratio of the horizontal surface area of the floor of chamber 34 that overlaps rigid layer 35 to the horizontal surface area of chamber 38 that is under layer 35, and b is the ratio of the horizontal surface area of chamber 37 that is directly below rigid layer 35 to the horizontal surface area of chamber 38 that is under layer 35. Constant c is shown by the following equation:

$$c = M \cdot \frac{\Delta H}{H} \cdot \frac{A_{32}}{A_{38}} \quad (3)$$

where M is the bulk modulus of the elastomer layer, H is the vertical height of chamber 38 (FIG. 3) when $P_1$ is at ambient pressure, ΔH is change in the vertical height of chamber 38 when $P_1$ is increased above ambient pressure and layer 35 presses down on chamber 38, $A_{32}$ is the horizontal surface area of a cross section of elastomer layer 32 that is underneath layer 35 (within the dotted line 35 in FIG. 4B), and $A_{38}$ is the horizontal surface area of chamber 38 that is under layer 35.

Chamber 37 reduces the force with which elastomer material in layer 32 presses up against rigid material 35 when material 35 is forced downward (with respect to FIG. 3), preserving the pressure amplification effect on $P_2$. Pressure multiplier 30 is advantageous, because it can be microfabricated (e.g., less than 1 mm thick). Also, the fluid in input chamber 34 is isolated from the fluid in output chamber 38. This may be an advantage, because the fluids in the input and output chamber of a pressure multiplier may be different types of fluids.

Figure 4C:
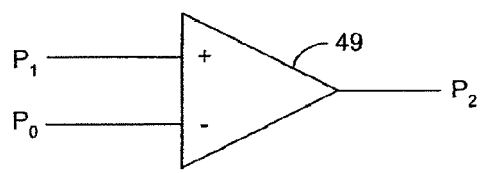
FIG. 4C is a symbol for a pressure multiplier.

FIG. 4C is a symbol for a pressure multiplier such as pressure multiplier 30. In a further embodiment, $P_0$ need not be ambient pressure, but may be any pressure level. In this embodiment the pressure amplification system of FIGS. 3 and 4A-4B amplifies the pressure difference between $P_1$ and $P_0$ according to the gain factor represented in equation (2) to provide pressure $P_2$ at the output. Microfluidic pressure multipliers of the present invention may be coupled with other microfluidic devices (that are discussed in further detail below) to build devices such that perform a variety of analog functions such as integration and differentiation using configurations known to those of skill in the semiconductor circuit art.

Microfabricated fluidic devices of the present invention also include devices that act as switches that may be turned ON and OFF. A fluidic switch is "open" during its ON state allowing fluid flow through the channel between the source and the drain. A fluidic switch is "closed" during its OFF state preventing fluid flow through the channel between the source and the drain. Microfluidic switches are opened and closed by changing the pressure in the gate of the switch. The pressure in the gate of the switch does not need to be increased above or reduced below the pressure in the drain-to-source channel. This provides an advantage, because microfluidic switches of the present invention can be coupled together to control each other on a single chip to perform complex logic, mathematical, multiplexing, and latching functions.

Figure 5A:
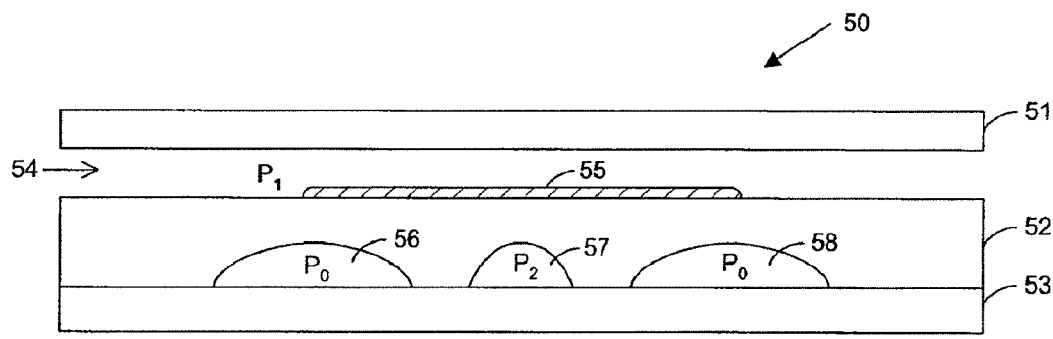
FIGS. 5A-5B and 6 show a first embodiment of a microfabricated fluidic switch.
Figure 5B:
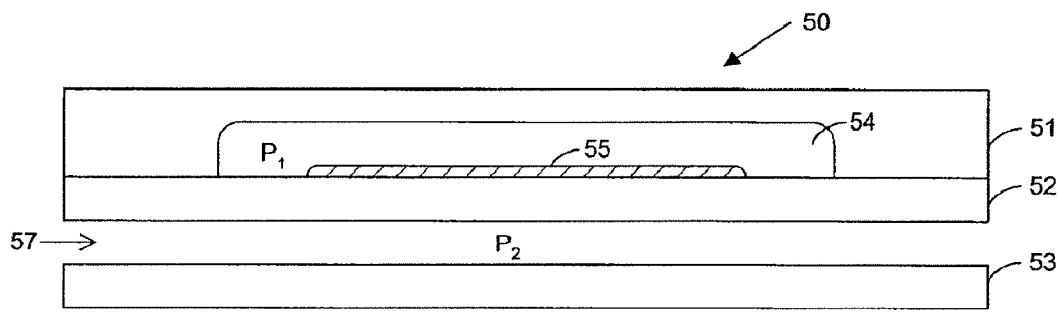
Figure 6:
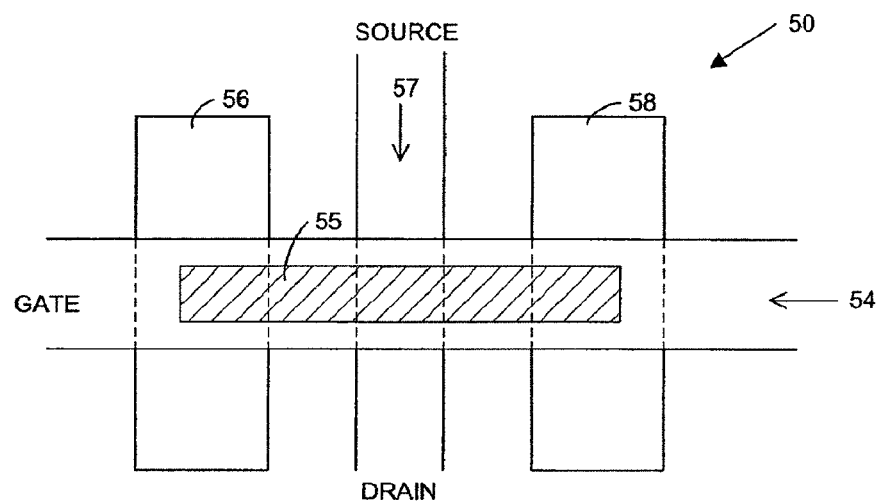

A first embodiment of a microfabricated fluidic switch is shown in FIGS. 5A-5B and 6. FIG. 6 is a top down view of fluidic switch 50, FIG. 5A is a cross sectional view of fluidic switch 50 along channel 54, and FIG. 5B is a cross sectional view of fluidic switch 50 along channel 57. Fluidic switch 50 includes substrate 53, elastomer layer 52, and elastomer layer 51 as shown in FIG. 5A. Elastomer layer 51 contains channel 54, and elastomer layer 52 contains channel 57 and chambers 56 and 58. Channel 54 is coupled to the gate of the switch. Channel 57 is coupled between the source and the drain of the switch. Layers 51-53 may be formed and hermetically sealed using methods described in further detail in PCT Patent Application Number PCT/US00/17740 mentioned above.

Layer 55 comprises a rigid material that is deposited on top of layer 52. Layer 51 may then be placed on top of layer 52 so that layer 55 is inside channel 54. Layer 55 is deposited on layer 52 so that it overlaps channel 57 and portions of chambers 56 and 58 as shown in FIG. 6. A fluid is passed through channel 54 at pressure $P_1$. A fluid is passed through channel 57 at pressure $P_2$. Channel 54 is perpendicular to channel 57. Chambers 56 and 58 contain fluid at ambient pressure $P_0$.

Layers 51-52 may be, for example, 1-1000 microns thick. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, and 1000 microns.

Chamber 54 may be, for example, 2.5-5000 microns wide. Specific examples include 2.5, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Channel 57 may be, for example, 0.1 micron-1 mm wide. Specific examples include 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, 100, 120, 140, 160, 180, 200, 250, 300, 350, 400, 450, 500, 550, 600, 650, 700, 750, 800, 850, 900, 950, and 1000 microns.

Layer 55 may be, for example, 1-100 microns thick. Specific examples include 1, 2, 3, 4, 5, 6, 7, 8, 9, 10, 20, 30, 40, 50, 60, 70, 80, 90, and 100 microns.

When the pressure $P_1$ in channel 54 is increased above $P_0$, the radius of channel 54 expands and rigid layer 55 moves downwardly (with respect to FIGS. 5A-5B) applying pressure against channel 57 and chambers 56 and 58. As $P_1$ increases, layer 55 presses down on the portion of channel 57 beneath layer 55 pinching channel 57 closed. Channel 57 is concave in shape making it more collapsible so that channel 57 makes a complete seal to completely block the flow of fluid there through when $P_1$ is increased to a predetermined level. Therefore, the device of FIGS. 5A-5B and 6 acts like a switch. The structure of FIG. 3 does not act like a switch. Channel 38 does not completely close when $P_1$ increases, because channel 38 is sealed at one end. Channel 57 is a flow through channel, because channel 38 is sealed at one end. Channel 57 is a flow through channel, while chamber 38 and channel 42 do not comprise a flow through channel.

Chambers 56 and 58 reduce the upward force that elastomer material in layer 52 applies to layer 55 when channel 54 expands so that channel 57 closes more quickly and completely. When channel 54 expands to close channel 57, fluid is displaced from chambers 56 and 58 beneath channel 54 into adjacent portions of chambers 56 and 58. Chambers 56 and 58 allow channel 57 to be closed without having to increase the pressure in gate channel 54 above the pressure in channel 57. Therefore, switch 50 may be coupled with other microfluidic switches to perform logic functions and other functions, because switch 50 does not require a pressure drop from the gate channel to the source-to-drain channel.

The microfabricated fluidic device of FIGS. 5A-5B and FIG. 6 functions as a switch that causes channel 57 to be open or closed. When pressure $P_1$ equals $P_0$, channel 57 is open and fluid can flow there through. When pressure $P_1$ is increased to a predetermined level in channel 54, channel 57 closes and the flow of fluid through channel 57 is blocked. Therefore, a fluidic switch is open when fluid is allowed to flow through a specific channel and closed when the flow of fluid through that channel is blocked.

Figure 7A:
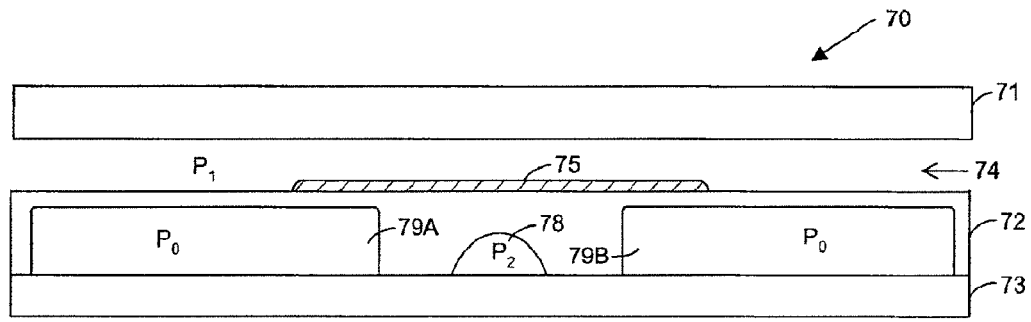
FIGS. 7A-7E show a second embodiment of a microfabricated fluidic switch.
Figure 7B:
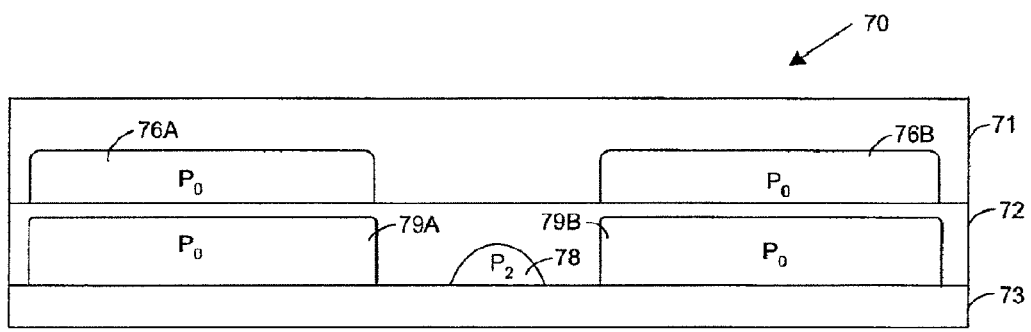
Figure 7C:
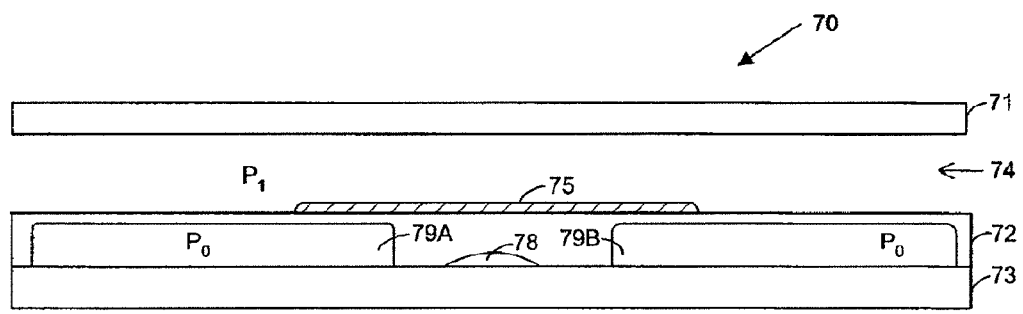
Figure 7D:
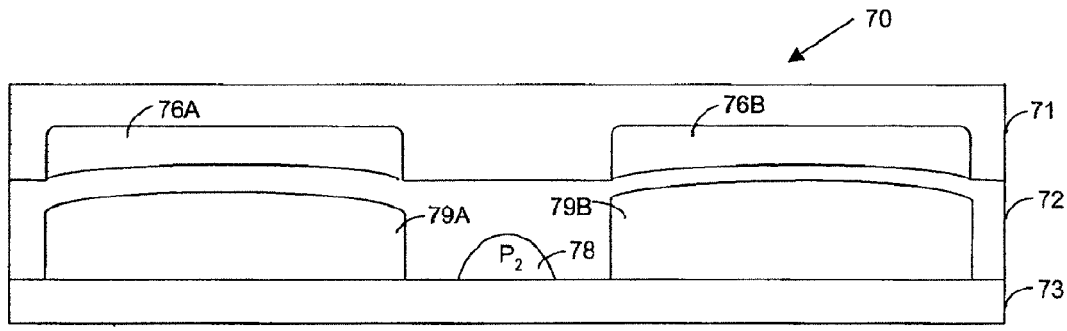
Figure 7E:
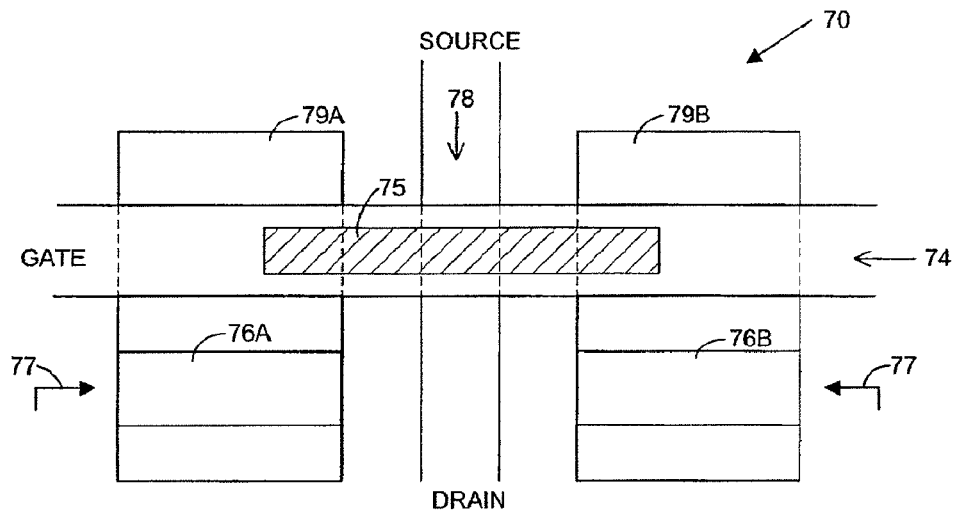

A second embodiment of a microfabricated fluidic switch is shown in FIGS. 7A-7E. FIGS. 7A-7D are cross sectional views of fluidic switch 70, and FIG. 7E is a top down view of fluidic switch 70. FIGS. 7A and 7C are cross sectional views along channel 74, and FIGS. 7B and 7D are cross sectional views along horizontal axis 77 illustrated in FIG. 7E. Switch 70 includes substrate 73, elastomer layer 72, and elastomer layer 71. Elastomer layer 71 contains channel 74, and elastomer layer 72 contains channel 78 and chambers 79A and 79B. Channel 74 is coupled to the gate of the switch. Channel 78 is coupled between the source and the drain of the switch. Layers 71-73 may be formed and hermetically sealed using methods described in further detail in PCT Patent Application Number PCT/US00/17740 mentioned above.

Layer 75 comprises a rigid material (such as PMMA) that is deposited on top of layer 72. Layer 71 can then be placed on top of layer 72 so that layer 75 is inside channel 74. Layer 75 is deposited on layer 72 so that it overlaps channel 78 and portions of chambers 79A-79B. A fluid is passed through channel 74 at pressure $P_1$. A fluid is passed through channel 78 at pressure $P_2$. Channel 74 is perpendicular to channel 78. Chambers 79A-79B contain fluid at ambient pressure $P_0$.

Layers 71-72 may be, for example, 1-1000 microns thick. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, and 1000 microns.

Channel 74 may be, for example, 2.5-5000 microns wide. Specific examples include 2.5, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Channel 78 may be, for example, 0.1 micron-1 mm wide. Specific examples include 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, 100, 120, 140, 160, 180, 200, 250, 300, 350, 400, 450, 500, 550, 600, 650, 700, 750, 800, 850, 900, 950, and 1000 microns.

Layer 75 may be, for example, 1-100 microns thick. Specific examples include 1, 2, 3, 4, 5, 6, 7, 8, 9, 10, 20, 30, 40, 50, 60, 70, 80, 90, and 100 microns.

When the pressure $P_1$ in channel 74 is increased above $P_0$, the radius of channel 74 expands and rigid layer 75 moves downwardly as shown in FIG. 7C applying pressure against channel 78 and chambers 79A-79B. As $P_1$ increases, layer 75 presses down on the portion of channel 78 beneath layer 75 pinching channel 78 closed. Channel 78 is concave in shape making it more collapsible so that channel 78 completely closes when $P_1$ is increased to a predetermined level.

Chambers 79A-79B reduce the upward force that elastomer material in layer 72 applies to layer 75 when channel 74 expands so that channel 78 closes more quickly and completely. When channel 74 expands to close channel 78, fluid is displaced from chambers 79A-79B beneath channel 74 into adjacent portions of chambers 79A-79B. Chambers 79A-79B provide less resistance to downward pressure on channel 78 than chambers 56 and 58, because chambers 79A-79B are wider than chambers 56 and 58.

Chambers 79A-79B allow channel 78 to be closed without having to increase the pressure in gate channel 74 above the pressure in channel 78. Therefore, switch 70 may be coupled with other microfluidic switches to perform logic functions and other functions, because switch 70 does not require a pressure drop from the gate channel to the source-to-drain channel.

When channel 78 is closed by increased pressure in channel 74, gas is displaced in chambers 79A-79B beneath channel 74 (shown in FIG. 7C) causing the pressure in chambers 79A-79B to increase. The increased pressure pushes up on air chambers 76A-76B as shown by the arrows in FIG. 7D. Air chambers 76A-76B are located over chambers 79A-79B, respectively, adjacent to channel 74 in FIG. 7E. Chambers 76A-76B contain fluid initially at ambient pressure. Chambers 76A-76B allow the volume of chambers 79A-79B to increase when air is displaced in chambers 79A-79B so that the increase in pressure in chambers 79A-79B is minimized. Channel 78 closes with less of a pressure increase in channel 74, because the pressure in chambers 79A-79B increases less.

In a further embodiment of the present invention, the structure shown in FIGS. 7A-7E may be configured as a vacuum actuated normally open microfluidic switch. In the present application, a "vacuum" may refer to zero pressure or any reduction in pressure from ambient. In this embodiment, chambers 79A-79B are coupled to the gate of the switch, channel 74 is filled with fluid at ambient pressure, and chambers 76A-76B are filled with fluid at ambient pressure. Channel 78 is coupled between the source and the drain of the switch. When the pressure in gate chambers 79A-79B is at ambient, drain-to-source channel 78 is open as shown in FIG. 7A. When the pressure in gate chambers 79A-79B is reduced (e.g., to a vacuum), rigid layer 75 is pulled down, closing source-to-drain channel 78 as shown in FIG. 7C.

Figure 8:
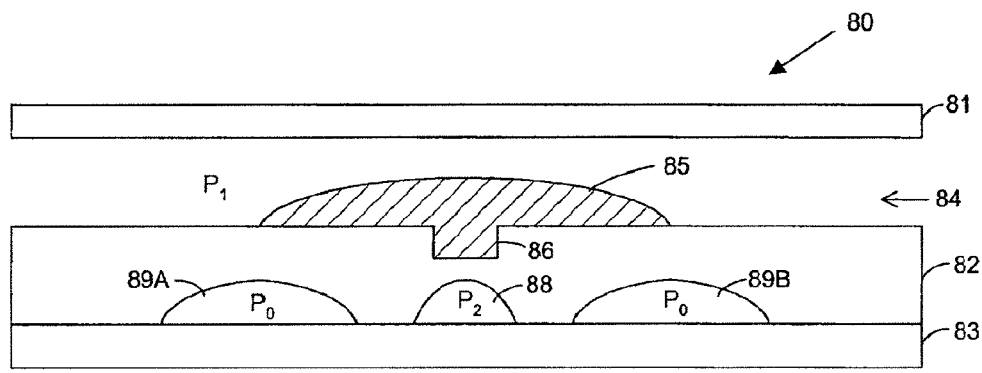
FIG. 8 shows a third embodiment of a microfabricated fluidic switch.

A third embodiment of a microfabricated fluidic switch is shown in FIG. 8. Fluidic switch 80 comprises substrate 83 and elastomer layers 81 and 82. FIG. 8 is a cross sectional view of switch 80 across channel 84. Channel 84 is coupled to the gate of the switch. Layer 82 comprises channel 88 and chambers 89A and 89B. Channel 88 is coupled between the drain and the source of the switch. Rigid material 85 is deposited inside region 86 and on top of layer 82 as shown in FIG. 8.

When pressure $P_1$ in channel 84 increases, rigid layer 85 moves downwardly, closing channel 88. The extension of rigid layer 85 into region 86 facilitates the closing of channel 88 by more effectively concentrating the force applied by layer 85 directly over drain-to-source channel 88. Chambers 89A-89B allow channel 88 to be closed without having to increase the pressure in gate channel 84 above the pressure in channel 88. Therefore, switch 80 may be coupled with other microfluidic switches to perform logic functions and other functions, because switch 80 does require a pressure drop from the gate channel to the source-to-drain channel.

Layers 81-82 may be, for example, 1-2000 microns thick. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, and 2000 microns.

Chamber 84 may be, for example, 2.5-5000 microns wide. Specific examples include 2.5, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Channel 88 may be, for example, 0.1 micron-1 mm wide. Specific examples include 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, 100, 120, 140, 160, 180, 200, 250, 300, 350, 400, 450, 500, 550, 600, 650, 700, 750, 800, 850, 900, 950, and 1000 microns.

Layer 85 may be, for example, 1-2000 microns thick. Specific examples include 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, and 2000 microns.

In a further embodiment of the present invention, rigid material 35/55/75 may be eliminated from the structures of FIGS. 3-7, because the elastomer layer itself may be rigid enough to provide leverage. However, the rigid layer increases the Young's modulus to provide a better mechanical advantage.

An embodiment of a microfabricated fluidic switch that is normally closed, but opens when the pressure in the gate is increased is shown in FIGS. 9A-9D. This is called a pressure actuated normally closed switch. The switches of FIGS. 5A-8 are pressure actuated normally open switches, in which pressure is increased in the gate to close the switch.

Figure 9A:
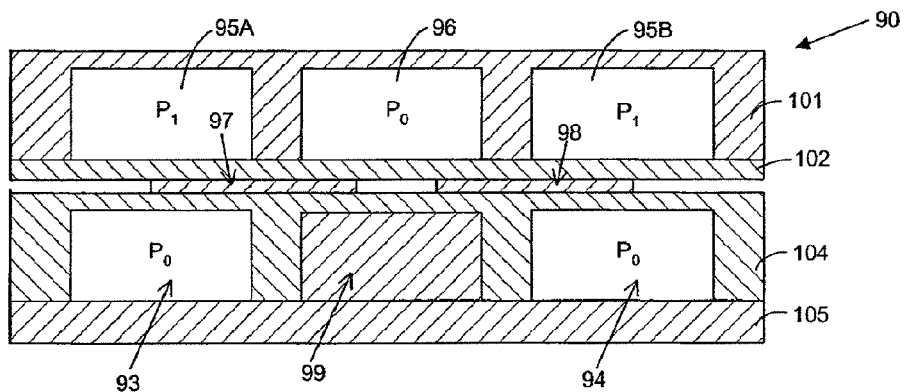
FIGS. 9A-9D show an embodiment of a microfabricated fluidic switch that is normally closed, but opens when the pressure in the gate is increased.
Figure 9B:
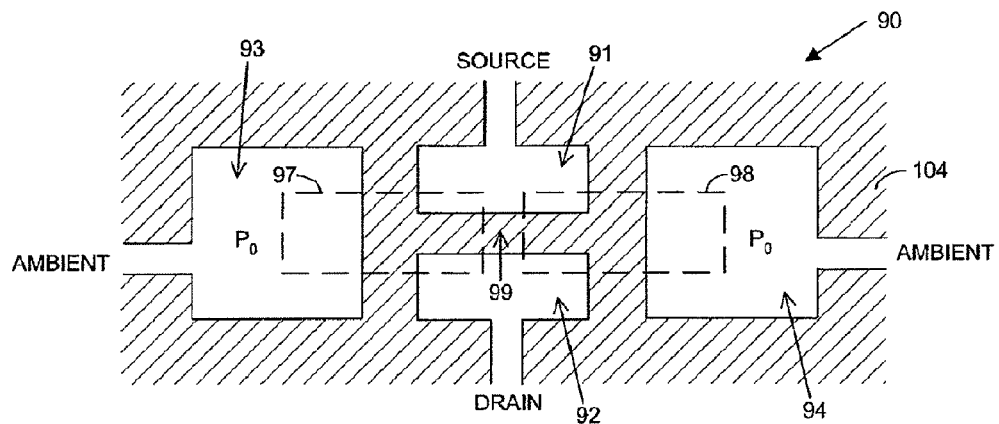
Figure 9C:
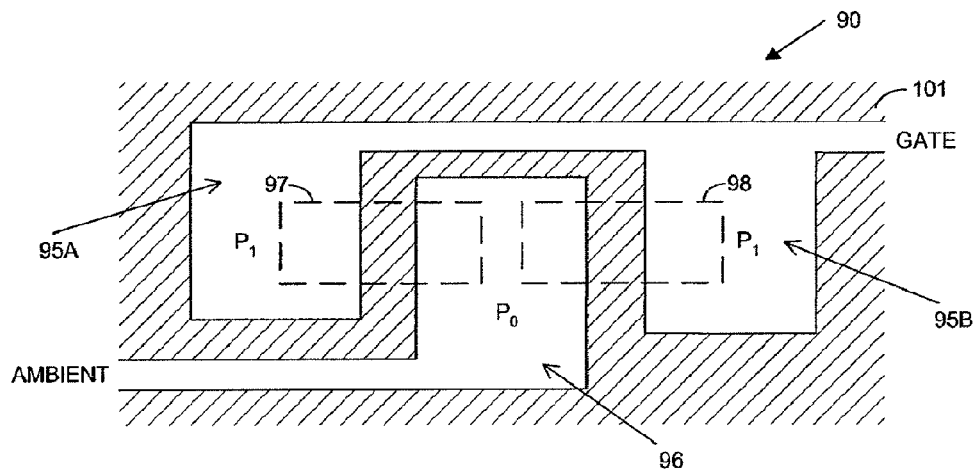

FIG. 9A is a cross sectional view of pressure actuated normally closed switch 90 which includes elastomer layers 101, 102, and 104 and substrate 105. FIG. 9B is a top down view of elastomer layer 104, and FIG. 9C is a top down view of elastomer layer 101. Rigid material is deposited in regions 97 and 98 on layer 104, and layer 102 is placed on top of regions 97 and 98.

Empty space exists between layers 102 and 104 adjacent to regions 97-98. Fluid is introduced into chambers 93, 94, and 96 at ambient pressure $P_0$.

Chambers 95A and 95B are coupled together and to the gate of the switch through openings. Fluid is introduced into chambers 95A-95B at pressure $P_1$. Layer 104 has elastomer bar region 99 which is not sealed to substrate 105. Bar region 99 is located between source chamber 91 and drain chamber 92 as shown in FIG. 9B. Rigid regions 97 and 98 lie above portions of bar region 99 and chambers 93 and 94. Rigid regions 97 and 98 also lie below chambers 95A-95B and 96.

Layers 101 and 104 may be, for example, 1-1000 microns thick. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, and 1000 microns.

Chambers 93, 94, 95A-95B, and 96 may be, for example, 2.5-5000 microns wide. Specific examples include 2.5, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Layers 97-98 may be, for example, 1-100 microns thick. Specific examples include 1, 2, 3, 4, 5, 6, 7, 8, 9, 10, 20, 30, 40, 50, 60, 70, 80, 90, and 100 microns.

Figure 9D:
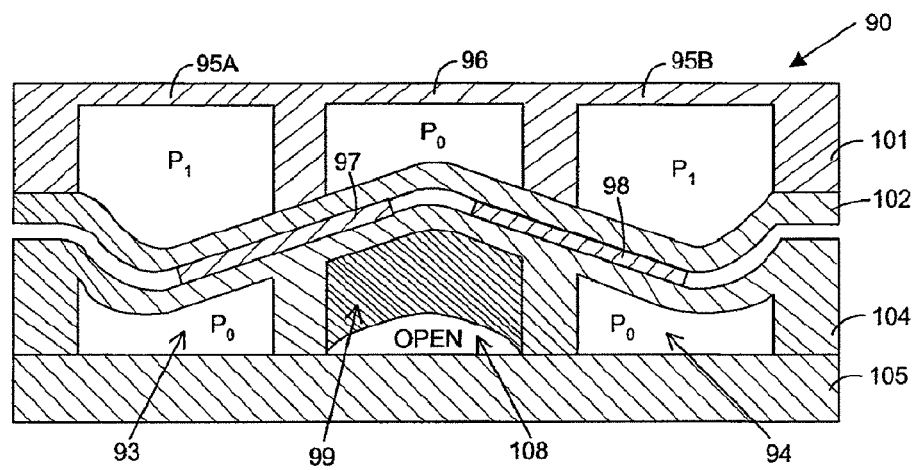

When pressure $P_1$ in chambers 95A-95B equals pressure $P_0$, bar region 99 lies flush against substrate 105 as shown in FIG. 9A and the channel between the source and the drain of switch 90 is closed. Thus, switch 90 is normally closed. When pressure $P_1$ is increased above $P_0$, chambers 95A-95B expand, pushing layers 102 and 104 down into chambers 93-94 as shown in FIG. 9D. Rigid regions 97-98 act as levers which are pushed upward into chamber 96 along with adjacent portions of layers 102 and 104.

Bar region 99 is pulled up with layer 104, causing chamber 108 to open underneath bar region 99. Chamber 108 is an opening that connects source chamber 91 to drain chamber 92. Thus, the channel between the drain and the source of switch 90 opens when $P_1$ is increased, and fluid may flow there between. Thus, switch 90 opens when pressure $P_1$ in chambers 95A-95B is increased to a predetermined value sufficient to lift up region 99.

Chambers 93, 94, and 96 allow channel 108 to be opened without having to increase the pressure in gate channel 95A/B above the pressure in channel drain chamber 92 and source chamber 91. Therefore, switch 90 may be coupled with other microfluidic switches to perform logic functions and other functions, because switch 90 does not require a pressure drop from the gate channel to the source-to-drain channel.

In a further embodiment of the present invention, the structures shown in FIGS. 9A-9D may be configured as vacuum actuated normally closed microfluidic switch. Chambers 93, 94, and 96 are coupled to the gate of the switch. Fluid in chambers 95A-95B is at ambient pressure. When the fluid in chambers 93, 94 and 96 are at ambient pressure, the switch is closed as shown in FIG. 9A. When the pressure of the fluid in chambers 93, 94, and 96 is reduced below ambient (e.g., to a vacuum), layers 97-98 act as levers to pull up region 99, opening channel 108 between drain chamber 92 and source chamber 91 as shown in FIG. 9D.

Figure 10:
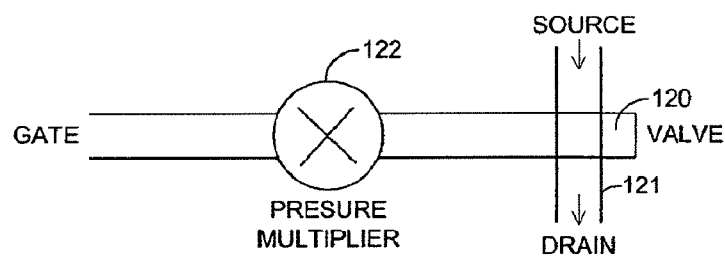
FIG. 10 illustrates a microfabricated fluidic switch comprising a pressure multiplier and a valve.

FIG. 10 illustrates a microfabricated fluidic switch comprising a pressure multiplier and a valve. FIG. 10 illustrates that a microfluidic switch may be formed by coupling a pressure multiplier to the control channel of a microfluidic valve. Pressure multiplier 122 may comprise the pressure multiplier of FIGS. 3 and 4A-4B. Pressure multiplier 122 is coupled to valve 120 which overlies drain-to-source channel 121. When pressure is increased at the gate in FIG. 10, the gate pressure is amplified by multiplier 122 and applied to valve 120.

Valve 120 presses down on channel 121 to completely close channel 121, so that fluid does not flow between the source and the drain. If desired, valve 120 and channel 121 may comprise previously known fluidic systems. Pressure multiplier 122 provides enough pressure in valve 120 so that channel 121 is opened and closed as a switch. Pressure multiplier 122 allows the source-to-drain channel to be opened and closed without increasing the pressure at the gate above the pressure in the source-to-drain channel. This allows switches formed as shown in FIG. 10 to be coupled together to form logic functions and complex other functions, because these switches do not require a pressure drop from the gate channel to the source-to-drain channel.

Figure 11A:
FIGS. 11A-11K show symbols representing microfabricated fluidic devices.
Figure 11B:
Figure 11C:
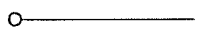
Figure 11D:
Figure 11E:
Figure 11F:
Figure 11G:
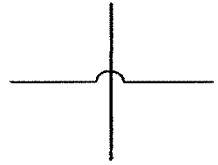

Symbols representing microfabricated fluidic devices are shown in FIGS. 11A-11K. The symbol of FIG. 11A represents a low flow resistance channel. The symbol of FIG. 11B represents a high flow resistance such as a long or a constricted channel. A fluidic resistor acts similar to an electrical resistor. A fluidic resistor exists when there is a high pressure difference between two terminals and a low flow between them. The symbol of FIG. 11C represents a channel terminal. The symbol of FIG. 11D represents a high pressure source. The symbol of FIG. 11E represents an ambient exhaust terminal. The symbol of FIG. 11F represents a node where channels connect. The symbol of FIG. 11G represents two channels that cross but do not connect.

Figure 11H:
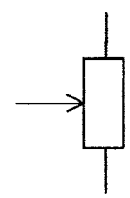
Figure 11I:
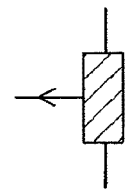
Figure 11J:
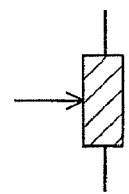
Figure 11K:
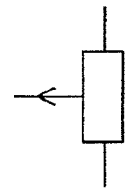

The symbol of FIG. 11H represents a pressure actuated normally open switch in which the pressure in the gate chamber is increased above ambient pressure to a high pressure in order to close the switch. The symbol of FIG. 11I represents a vacuum actuated normally closed switch in which the pressure in the gate chamber is reduced from ambient pressure to a vacuum to open the switch. The symbol of FIG. 11J represents a pressure actuated normally closed switch in which the pressure in the gate chamber is increased from ambient pressure to a high pressure to open the switch (such as switch 90). The symbol of FIG. 11K represents a vacuum actuated normally open switch in which the pressure in the gate chamber is reduced from ambient pressure to a vacuum to close the switch.

Microfabricated fluidic devices of the present invention may be connected together to form logic gates that perform logic functions and Boolean algebra. Previously known microfluidic chips often perform logic functions off-chip using electrical circuitry and then rout the output signal onto the microfluidic chip through macroscopic control lines which are cumbersome and take up a lot of space. Performing logic functions on chip using microfluidic logic gates can greatly reduce the number control lines routed onto the chip which advantageously saves space.

The bistable logic levels for the microfluidic logic gates are high pressure (HIGH) and low pressure (LOW). Each logic gate has a connection to a low pressure source (e.g., ambient pressure), and a connection to a high pressure source (e.g., at higher than ambient pressure). In an alternate embodiment, each logic gate has a connection to ambient pressure and a connection to a vacuum. In this embodiment, HIGH refers to the vacuum and LOW refers to ambient pressure.

All Boolean functions can be constructed entirely from NAND gates or entirely from NOR gates. A NAND gate performs an AND function on a set of inputs and inverts the output. A NOR gate performs an OR function on a set of inputs and inverts the output.

Figure 12A:
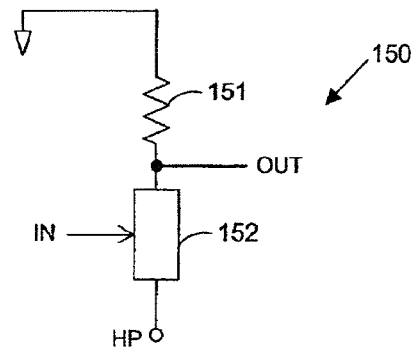
FIG. 12A shows an example of an inverter formed with microfabricated fluidic devices.

An example of an inverter formed with microfabricated fluidic devices is shown in FIG. 12A. Fluidic inverter 150 is a logic gate that accepts an input at IN and inverts it to provide an output OUT. OUT is the opposite logic state of IN. For example, if IN is HIGH, OUT is LOW, and if IN is LOW, OUT is HIGH. Inverter 150 comprises microfluidic resistor 151 coupled between ambient exhaust and OUT, and pressure actuated normally open microfluidic switch 152 which is coupled between OUT and a high pressure terminal. Input IN is coupled to the gate of switch 152.

Figure 12B:
FIG. 12B shows the symbol for an inverter.

When IN is LOW, switch 152 is open, and fluid is allowed to flow from the high pressure terminal HP through resistor 151 to the ambient exhaust. The resistance of the channel of switch 152 is substantially less than the resistance of resistor 151. Therefore, OUT rises to the high pressure level at terminal HP. When IN is HIGH (i.e., high pressure), switch 152 is closed, and the flow of fluid through switch 152 is impeded. The pressure at OUT diffuses through resistor 151 to the ambient exhaust terminal, and OUT returns to LOW (i.e., ambient pressure). The symbol for an inverter is shown in FIG. 12B. Of course, other configurations for the construction of an inverter known to those of skill in the semiconductor circuit design art may be used to design a fluidic inverter in which transistors are replaced with fluidic switches.

Figure 12C:
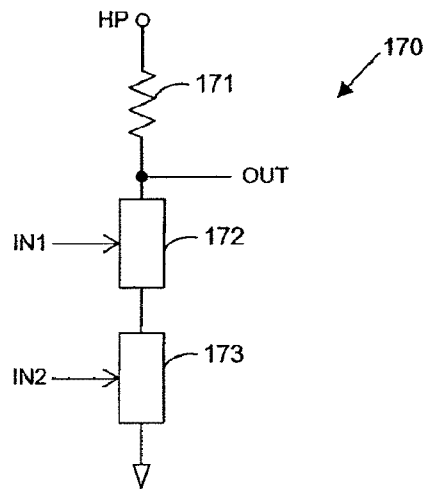
FIG. 12C shows an example of an OR logic gate formed with microfabricated fluidic devices.

An example of an OR logic gate formed with microfabricated fluidic devices is shown in FIG. 12C. OR gate 170 includes microfluidic resistor 171 coupled between a high pressure terminal and the output OUT. OR gate 170 also includes pressure actuated normally open microfluidic switches 172 and 173 which are coupled in series between OUT and an ambient pressure exhaust terminal. The gate of switch 172 is coupled to input IN1, and the gate of switch 173 is coupled to input IN2. When either of inputs IN1 or IN2 is at high pressure (HIGH), switch 172 or switch 173 is closed, and OUT is decoupled from the ambient exhaust terminal. The pressure at OUT rises to a high pressure (HIGH) as fluid flows from the high pressure terminal through resistor 171 to OUT. When both inputs IN1 and IN2 are at a low pressure (i.e., ambient pressure), switches 172 and 173 are both open and fluid flows from the high pressure terminal to the ambient exhaust terminal. The pressure at OUT decreases to ambient pressure (LOW), because the resistance of resistor 171 is much greater than the resistance of switches 172 and 173.

Figure 12D:
FIG. 12D shows the symbol for an OR gate.

Microfluidic OR gates may comprises any number of input terminals greater than one. Each input terminal is coupled to the gate of an additional switch that is coupled in series between OUT and the ambient exhaust terminal with switches 172 and 173. Of course, other configurations for the construction of OR logic gates known to those of skill in the semiconductor circuit design art may be used to design a microfluidic OR gate in which transistors are replaced with microfluidic switches. The symbol for an OR gate is shown in FIG. 12D. The truth table for OR gate 170 is shown in Table 1:

TABLE 1

| IN1 | IN2 | OUT |
|---|---|---|
| H | H | H |
| H | L | H |
| L | H | H |
| L | L | L |

Figure 12E:
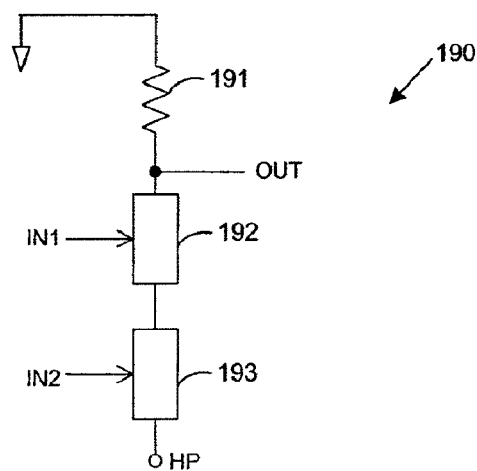
FIG. 12E is an example of a NOR logic gate formed with microfabricated fluidic devices.

An example of a NOR logic gate formed with microfabricated fluidic devices is shown in FIG. 12E. NOR gate 190 is formed by reversing the high pressure and ambient terminals in OR gate 170. NOR gate 190 includes microfluidic resistor 191 which is coupled between an ambient exhaust terminal and output OUT. NOR gate 191 also includes pressure actuated normally open microfluidic switches 192 and 193 which are coupled together in series between OUT and a high pressure terminal. The gate of switch 192 is coupled to input IN1, and the gate of switch 193 is coupled to input IN2.

When either of inputs IN1 or IN2 is at high pressure (HIGH), switch 192 or switch 193 is closed, and OUT is decoupled from the high pressure terminal. Fluid flows from OUT through resistor 191 to the ambient exhaust terminal, causing the pressure at OUT to be at ambient pressure (LOW). When both inputs IN1 and IN2 are at low ambient pressure, both of switches 192 and 193 are open and fluid flows from the high pressure terminal to the ambient exhaust terminal through resistor 191. The pressure at OUT rises to a HIGH level, because the resistance of resistor 191 is much greater than the resistance of switches 192 and 193.

Figure 12F:
FIG. 12F shows the symbol for a two input NOR gate.

Microfluidic NOR gates may comprise any number of input terminals greater than one. Each input terminal is coupled to the gate of an additional switch that is coupled in series between OUT and the high pressure terminal HP with switches 192 and 193. Of course, other configurations for the construction of NOR logic gates known to those of skill in the semiconductor circuit design art may be used to design a microfluidic NOR gate in which transistors are replaced with microfluidic switches. The symbol for a two input NOR gate is shown in FIG. 12F. The truth table for a two input NOR gate is shown below in Table 2:

TABLE 2

| IN1 | IN2 | OUT |
|---|---|---|
| H | H | L |
| H | L | L |
| L | H | L |
| L | L | H |

An example of an AND logic gate formed with microfabricated fluidic devices is shown in FIG. 12G. AND gate 210 includes microfluidic resistor 211 coupled between a high pressure terminal HP and output terminal OUT. AND gate 210 also includes pressure actuated normally open microfluidic switches 212 and 213 that are coupled in parallel between OUT and an ambient exhaust terminal. The gate of switch 212 is coupled to input terminal IN1, and the gate of switch 213 is coupled to input terminal IN2.

When either of input terminals IN1 or IN2 is at a low ambient pressure (LOW), one of switches 212 or 213 is open, and fluid flows from high pressure terminal HP to the ambient exhaust terminal through the open switch(es) and resistor 211. The pressure at OUT is LOW at ambient pressure, because the resistance of resistor 211 is much greater than the resistance of switches 212 and 213. When both of input terminals IN1 and IN2 are at high pressure (HIGH), both of switches 212 and 213 are closed blocking the flow of fluid from OUT to the ambient exhaust. Fluid now flows only from the high pressure terminal HP to OUT through resistor 211, causing the pressure at OUT increases to a high pressure (HIGH).

A microfluidic AND gate may comprises any number of inputs greater than one. Each input terminal is coupled to the gate of a normally open switch coupled in parallel with switches 212 and 213 between OUT and the ambient exhaust terminal. Of course, other configurations for the construction of AND logic gates known to those of skill in the semiconductor circuit design art may be used to design a microfluidic AND gate in which transistors are replaced with microfluidic switches. The symbol for a two input AND gate is shown in FIG. 12H. The truth table for a two input AND gate is shown in Table 3 below:

TABLE 3

| IN1 | IN2 | OUT |
|-----|-----|-----|
| H | H | H |
| H | L | L |
| L | H | L |
| L | L | L |

An example of a NAND logic gate formed with microfabricated fluidic switches is shown in FIG. 12I. NAND gate 230 is formed by reversing the high pressure HP and ambient exhaust terminals of AND gate 210. NAND gate 230 includes microfluidic resistor 231 which is coupled between an ambient exhaust terminal and output terminal OUT. NAND gate 230 also includes pressure actuated normally open microfluidic switches 232 and 233 which are coupled in parallel between OUT and high pressure terminal HP. The gate of switch 232 is coupled to input terminal IN1, and the gate of switch 233 is coupled to input terminal IN2.

When either of inputs IN1 or IN2 are at ambient pressure (LOW), one of switches 232 or 233 is open, and fluid flows from the HP terminal to the ambient exhaust through the open switch(es) and resistor 231. The pressure at OUT increases to high pressure (HIGH), because the resistance of resistor 231 is greater than the resistance of switches 232 and 233. When both inputs IN1 and IN2 are at high pressure (HIGH), both of switches 232 and 233 are closed and fluid flow to the HP terminal is blocked. The pressure at OUT diffuses through resistor 231 to the ambient exhaust terminal causing the pressure at OUT to decrease to ambient pressure (LOW).

A microfluidic NAND gate may comprise any number of input terminals greater than one. Each input terminal is coupled to the gate of a normally open switch coupled in parallel with switches 232 and 233 between OUT and the HP terminal. Of course, other configurations for the construction of NAND logic gates known to those of skill in the semiconductor circuit design art may be used to design a microfluidic NAND gate in which transistors are replaced with microfluidic switches. The symbol for a two input NAND gate is shown in FIG. 12J. The truth table for a two input NAND gate is shown in Table 4 below:

TABLE 4

| IN1 | IN2 | OUT |
|-----|-----|-----|
| H | H | L |
| H | L | H |
| L | H | H |
| L | L | H |

Microfabricated fluidic devices of the present invention may also be used to construct Set-Reset (S-R) flip-flops (also called latches) that have the same truth table as S-R flips-flops constructed from electronic circuits. Flip-flop 250 in FIG. 13 is one example of an S-R flip-flop that is constructed with two cross-coupled NAND gates 251 and 252. NAND gate 251 has a first input terminal $\overline{SET}$ and a second input terminal coupled to the output terminal $\overline{OUT}$ of NAND gate 252. NAND 252 has a first input terminal $\overline{RESET}$ and a second input terminal coupled to the output terminal OUT of NAND gate 251.

Flip-flop 250 operates as follows. A transitory LOW signal occurs when the $\overline{SET}$ or $\overline{RESET}$ input transitions from high pressure (HIGH) to ambient pressure (LOW) and then transitions back to high pressure (HIGH) again. When a transitory LOW occurs on the $\overline{SET}$ input, OUT goes HIGH and remains HIGH. When a transitory LOW signal occurs on the $\overline{RESET}$ input, $\overline{OUT}$ goes HIGH and remains HIGH. When the pressure at the $\overline{SET}$ and $\overline{RESET}$ inputs are both HIGH, outputs OUT and $\overline{OUT}$ remain in their previous states. An unstable condition exists at outputs OUT and $\overline{OUT}$ when the pressure at the $\overline{SET}$ and $\overline{RESET}$ inputs are both LOW.

Figure 14A:
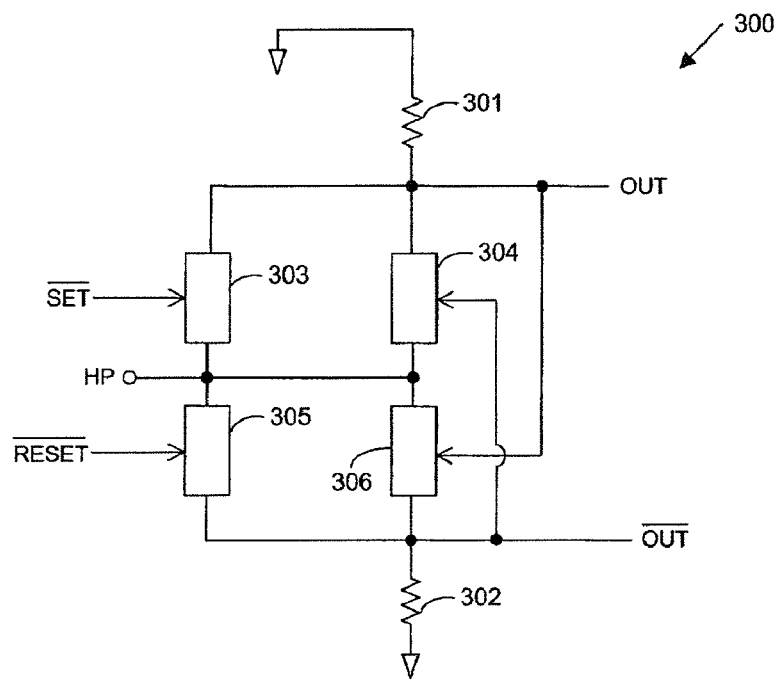
FIG. 14A shows an example of a S-R flip-flop of the present invention constructed with microfabricated fluidic cross-coupled NAND gates.

An example of a S-R flip-flop of the present invention constructed with microfabricated fluidic cross-coupled NAND gates is shown in FIG. 14A. Flip-flop 300 include fluidic resistor 301 which is coupled between a first ambient exhaust terminal and output terminal OUT, and fluidic resistor 302 which is coupled between a second ambient exhaust terminal and output $\overline{OUT}$. Flip-flop 300 also includes pressure actuated normally open microfluidic switches 303 and 304 that are coupled in parallel between OUT and a high pressure terminal HP, and pressure actuated normally open microfluidic switches 305 and 306 that are coupled in parallel between $\overline{OUT}$ and the HP terminal. The gate of switch 303 is coupled to input terminal $\overline{SET}$, the gate of switch 304 is coupled to the output terminal $\overline{OUT}$, the gate of switch 305 is coupled to input terminal $\overline{RESET}$, and the gate of switch 306 is coupled to output terminal OUT.

When the pressure at the $\overline{RESET}$ input remains HIGH and the pressure at the $\overline{SET}$ input transitions from HIGH to LOW, switch 305 is closed, switch 303 opens, and the pressure at OUT goes HIGH because it is coupled to the high pressure terminal HP through low resistance switch 303. Switch 306 is closed because OUT is HIGH, and the pressure at $\overline{OUT}$ goes LOW, because $\overline{OUT}$ is decoupled from the HP terminal. Switch 304 is open, because $\overline{OUT}$ is LOW. When the pressure at the $\overline{SET}$ input goes HIGH again, switch 303 closes. However, the pressure at OUT remains HIGH, because OUT is coupled to the HP terminal through switch 304 which remains open. The pressure at $\overline{OUT}$ remains LOW, because switch 306 remains closed.

When the pressure at the $\overline{SET}$ input remains HIGH and the pressure at the $\overline{RESET}$ input transitions from HIGH to LOW, switch 303 remains closed and switch 305 opens. The pressure at $\overline{OUT}$ goes HIGH, because $\overline{OUT}$ is coupled to the HP terminal through low resistance switch 305. Switch 304 is closed because $\overline{OUT}$ is HIGH, and the pressure at OUT goes LOW, because it is decoupled from the HP terminal. When the pressure at the $\overline{RESET}$ input goes HIGH again, switch 305 closes, but switch 306 remains open because OUT is LOW. Therefore, the pressure $\overline{OUT}$ remains HIGH keeping switch 304 closed, so that the pressure at OUT remains LOW.

When the pressures at $\overline{RESET}$ and $\overline{SET}$ are both HIGH, the pressures at OUT and $\overline{OUT}$ both remain at their previous logic states. The pressures at OUT and $\overline{OUT}$ are both HIGH when the pressures at $\overline{RESET}$ and $\overline{SET}$ are both LOW, which is considered an unstable output state because OUT and $\overline{OUT}$ cannot remain in that state when $\overline{\text{RESET}}$ or $\overline{\text{SET}}$ go HIGH. The truth table for flip-flop 300 is shown in Table 5.

TABLE 5

| SET | $\overline{\text{RESET}}$ | OUT | $\overline{\text{OUT}}$ |
|---|---|---|---|
| H to L to H | H | H | L |
| H | H to L to H | L | H |
| H | H | Previous State | Previous State |
| L | L | H | H |

Figure 14B:
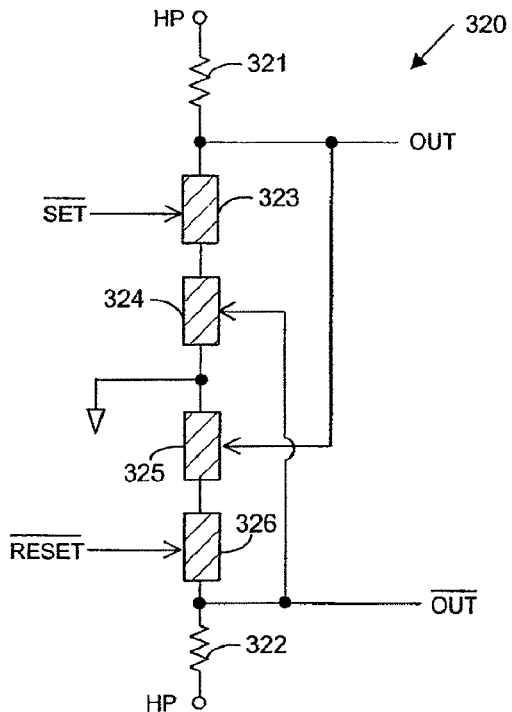
FIG. 14B shows another example of an S-R flip-flop of the present invention comprising microfabricated microfluidic devices.

Another example of an S-R flip-flop of the present invention comprising microfabricated microfluidic devices is shown in FIG. 14B. S-R flip-flop 320 includes fluidic resistor 321 that is coupled between a first high pressure terminal HP and output terminal OUT, and fluidic resistor 322 that is coupled between a second high pressure terminal HP and output terminal $\overline{\text{OUT}}$. S-R flip-flop 320 also includes pressure actuated normally closed microfluidic switches 323 and 324 that are coupled in series between OUT and an ambient exhaust terminal, and pressure actuated normally closed microfluidic switches 325 and 326 that are coupled in series between $\overline{\text{OUT}}$ and the ambient exhaust terminal. The gate of switch 323 is coupled to the $\overline{\text{SET}}$ input, the gate of switch 324 is coupled to the $\overline{\text{OUT}}$ output, the gate of switch 325 is coupled to the OUT output, and the gate of switch 326 is coupled the $\overline{\text{RESET}}$ input.

When the pressure at the $\overline{\text{RESET}}$ input remains HIGH and the pressure at the $\overline{\text{SET}}$ input transitions from HIGH to LOW, switch 326 is open and switch 323 closes. The OUT terminal is decoupled from the ambient exhaust terminal, and fluid flows through resistor 321 until the pressure at OUT goes HIGH. Switch 325 opens when OUT goes HIGH. The pressure at $\overline{\text{OUT}}$ goes LOW, because $\overline{\text{OUT}}$ is coupled to the ambient exhaust terminal through switches 325 and 326 which have a much smaller resistance than resistor 322. Switch 324 is closed, because $\overline{\text{OUT}}$ is LOW. When the pressure at the $\overline{\text{SET}}$ input goes HIGH again, switch 323 opens. However, the pressure at OUT remains HIGH, because switch 324 remains closed continuing to decouple OUT from the ambient exhaust terminal. The pressure at $\overline{\text{OUT}}$ remains LOW, because switch 325 remains open.

When the pressure at the $\overline{\text{SET}}$ input remains HIGH and the pressure at the $\overline{\text{RESET}}$ input transitions from HIGH to LOW, switch 323 remains open and switch 326 closes. The pressure at $\overline{\text{OUT}}$ goes HIGH, because $\overline{\text{OUT}}$ is decoupled from the ambient exhaust terminal and coupled to the HP terminal through resistor 322. Switch 324 is open because $\overline{\text{OUT}}$ is HIGH. The pressure at OUT goes LOW, because it is coupled to the ambient exhaust terminal through low resistance switches 323 and 324 which are both open. When the pressure at the $\overline{\text{RESET}}$ input goes HIGH again, switch 326 opens, but switch 325 remains closed because OUT is LOW. Therefore, the pressure $\overline{\text{OUT}}$ remains HIGH keeping switch 324 open, so that the pressure at OUT remains LOW.

When the pressures at $\overline{\text{RESET}}$ and $\overline{\text{SET}}$ are both HIGH, the pressures at OUT and $\overline{\text{OUT}}$ both remain at their previous logic states. The pressures at OUT and $\overline{\text{OUT}}$ are both HIGH when the pressures at $\overline{\text{RESET}}$ and $\overline{\text{SET}}$ are both LOW, which is considered an unstable output state because OUT and $\overline{\text{OUT}}$, because OUT and $\overline{\text{OUT}}$ cannot remain in that state when $\overline{\text{RESET}}$ or $\overline{\text{SET}}$ go HIGH. The truth table for latch 320 is shown in Table 5.

Microfabricated fluidic S-R flip-flops can be used to provide a large number of arbitrary latched control signals from a small number of control lines that are multiplexed externally. Thus, having fluidic devices that perform the function of S-R flip-flips on the fluidic chip also greatly reduces the number of control lines that need to be brought onto the chip from external sources, providing additional space saving.

Further embodiments of the present invention include microfluidic vacuum actuated normally closed switches. Each of the valves discussed below with respect to FIGS. 15A-15J may be used as vacuum actuated normally closed switches when its input channel is coupled to a pressure amplifier such as pressure amplifier 30 (FIGS. 3 and 4A-4B) as shown for example in FIG. 10. Pressure applied to the gate of the resulting switch is amplified in the input channel of the valve. By adding a pressure amplifier to the input channel of one of the valves in FIGS. 15A-15J, the pressure in the gate of the resulting switch does not need to be decreased below the pressure in the output channel between the source and the drain of the switch. Therefore, by adding pressure multipliers to the valves of FIGS. 15A-15J, the resulting switches may be coupled together to perform logic functions and Boolean algebra as discussed above.

Figure 15A:
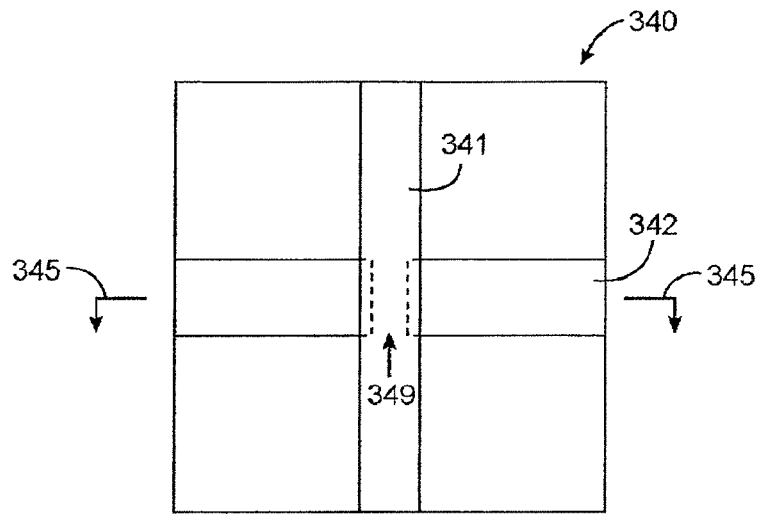
FIGS. 15A-15J are valves that may be used as vacuum actuated normally closed switches when its input channel is coupled to a pressure amplifier.

Valve 340 shown in FIG. 15A may be a microfluidic vacuum actuated normally closed switch when the gate is coupled to a pressure multiplier (as discussed with respect to FIG. 10). Valve 340 has channels 341 and 342 formed in elastomer block 347 on rigid substrate 348. Elastomer block 347 may comprise a plurality of elastomer layers sealed together. Channel 341 overlies and is perpendicular to channel 342. Channel 341 is the control channel, and channel 342 couples the source and the drain of the switch.

Figure 15B:
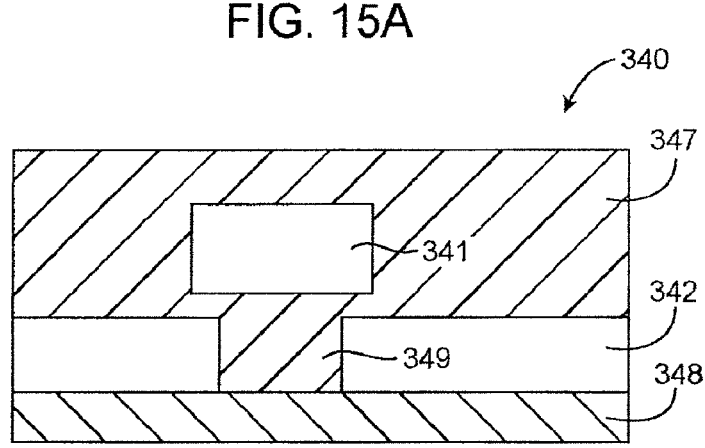
Figure 15C:
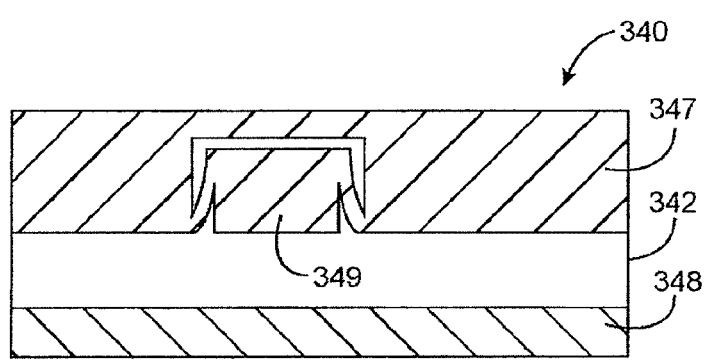

Cross sections of valve 340 along axis 345 are shown in FIGS. 15B-15C. Elastomer block 347 includes elastomer region 349 which extends into channel 342. The length of region 349 equals the width of channel 342. When the pressure in channel 341 is at ambient pressure, region 349 extends into channel 342 as shown in FIG. 15B. Region 349 completely blocks channel 342 preventing fluid from flowing there through, because region 349 fully fills the width of channel 342. Therefore, valve 340 is closed in its normal state when pressure in channel 341 is at ambient.

When the pressure in channel 341 is reduced (e.g., to a vacuum), region 349 retracts into channel 341 as shown in FIG. 15C, because of the pressure differential between channel 341 and channel 342. Channel 342 opens when region 349 retracts into channel 341. Fluid can now freely flow through channel 342. Thus, vacuum pressure in gate 341 of valve 340 causes the switch to open, and ambient pressure in gate 341 causes the switch to close.

Layer 347 may be, for example, 1-1000 microns thick. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, and 1000 microns.

Channels 341-342 may be, for example, 0.1-5000 microns wide. Specific examples include 0.1, 0.3, 0.5, 0.7, 1, 2, 2.5, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Figure 15D:
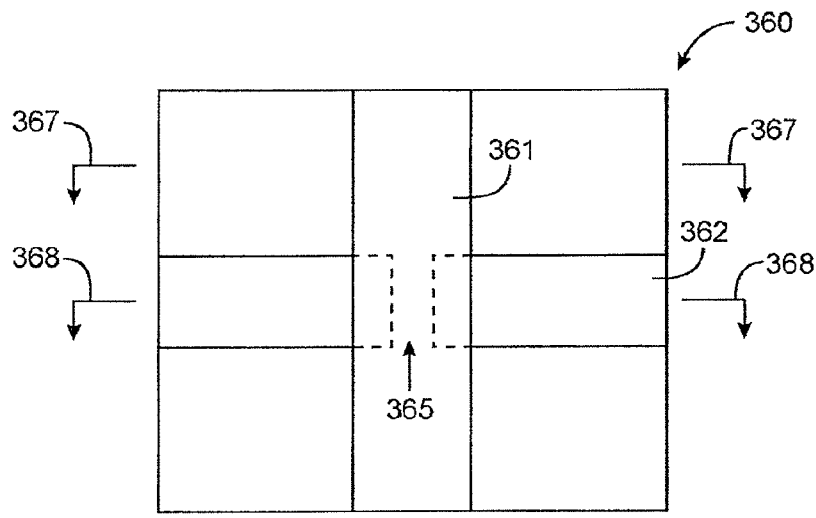

Valve 360 shown in FIG. 15D is a second embodiment of a valve that can be used as a vacuum actuated normally closed microfluidic switch if a pressure amplifier is coupled to the input channel 361. Valve 360 comprises an elastomer block 363 which may be formed from elastomer layers sealed together. Valve 360 has perpendicular channels 361 and 362. Channel 361 overlies channel 362. Channel 361 is the input channel of valve 360, and channel 362 couples the source and the drain of the switch.

Figure 15E:
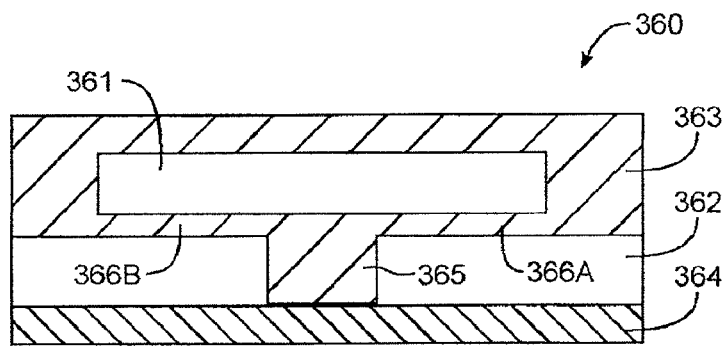
Figure 15F:
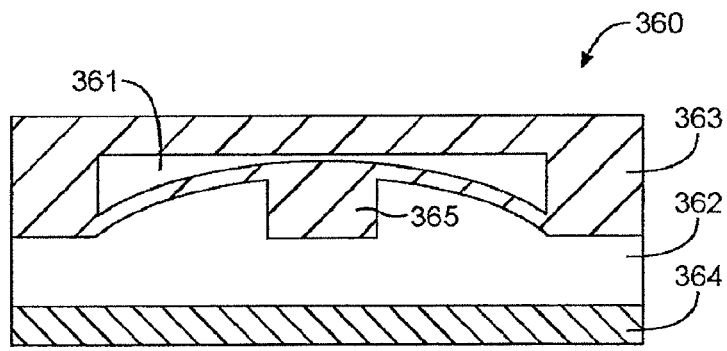

Cross sections of valve 360 are shown in FIGS. 15E-H. Elastomer 363 includes elastomer region 365 which extends down into channel 362. When the pressure in channel 361 is at ambient pressure, region 365 blocks channel 362 as shown in FIG. 15E, and valve 360 is closed, because region 365 extends across the width of channel 362. When the pressure in channel 361 is reduced (e.g., to a vacuum), region 365 retracts into channel 361 as shown in FIG. 15F, unblocking channel 362 so that valve 360 is open.

As can be seen by comparing FIGS. 15B and 15E, channel 341 is only slightly wider than region 349, while channel 361 is much wider than region 365. It is advantageous that channel 361 is much wider than channel region 365, because it takes less of a pressure reduction in channel 361 to retract region 365 into channel 361, than it does to retract region 349 into channel 341. This is because elastomer regions 366A-366B of block 363 are wide enough so that they do not have to stretch a lot to allow region 365 to retract into channel 361 relative to region 349.

Layer 363 may be, for example, 1-1000 microns thick. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, and 1000 microns.

Channels 361-362 may be, for example, 0.1-5000 microns wide. Specific examples include 0.1, 0.5, 1, 2, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Figure 15G:
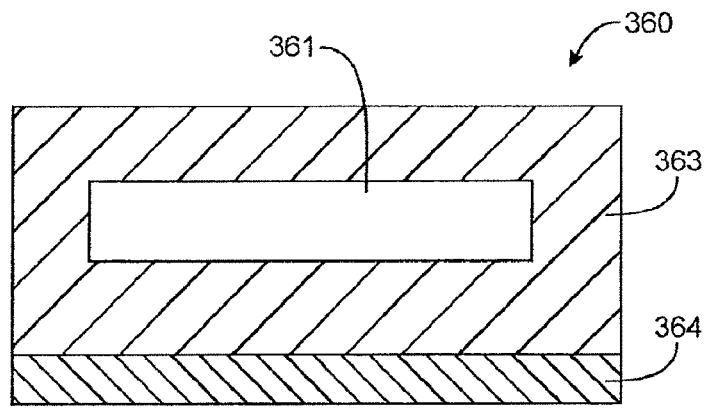
Figure 15H:
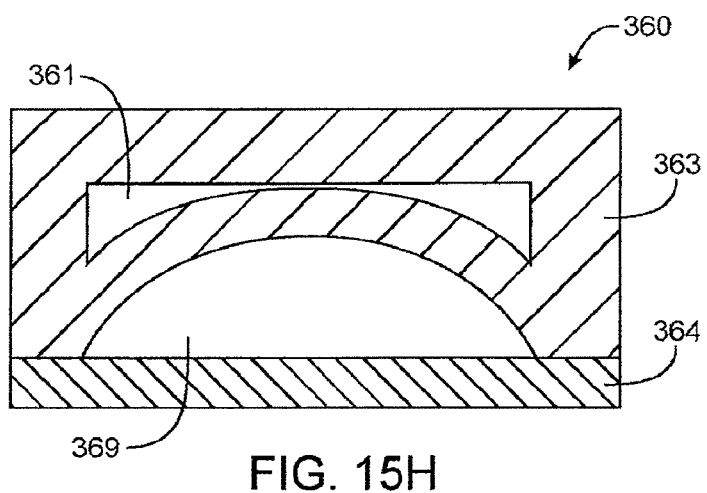

A disadvantage of valve 360 is illustrated in FIGS. 15G-15H. FIG. 15G is a cross section of valve 360 along horizontal axis 367 (FIG. 15D) when the pressure in channel 361 is at ambient pressure and valve 360 is closed. FIG. 15H is a cross section of valve 360 along axis 367 when the pressure in channel 361 is a vacuum and valve 360 is open. As can be seen in FIG. 15H, the portion of elastomer 363 under channel 361 retracts into channel 361 when the pressure in channel 361 is reduced (e.g., to a vacuum), opening up cross channel 369 below channel 361. Channel 369 is unwanted because fluid in channel 362 can leak out through channel 369, causing unwanted effects in valve 360. The same problem can occur in valve 340, beneath channel 341.

Figure 15I:
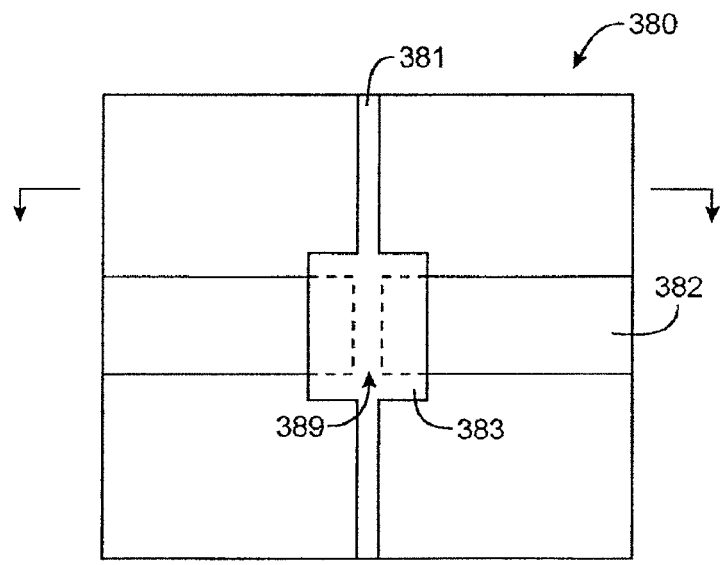
Figure 15J:
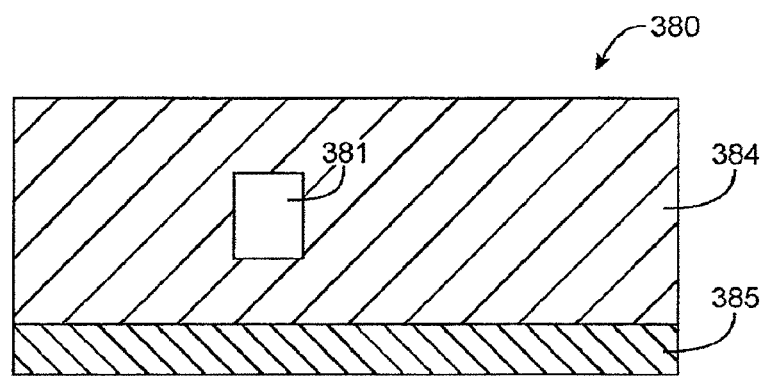

The problem illustrated in FIG. 15H can be minimized by reducing the width of the gate channel (except above the drain-source channel) as shown in FIG. 15I. In a further embodiment of the present invention, valve 380 shown in FIG. 15I may be used as a vacuum actuated normally open microfluidic switch if a pressure multiplier is coupled to its input channel 381. Valve 380 comprises elastomer block 384 on rigid substrate 385. Valve 380 has input channel 381, and channel 382 which couples the drain and the source together. Channels 381 and 382 are perpendicular to each other. Input channel 381 is relatively narrow except in region 383 over channel 382 where channel 381 widens. Thus, when the pressure in channel 381 is reduced (e.g., to a vacuum), elastomer 384 does not retract into the narrow portion of channel 381, as shown in FIG. 15J. Therefore, unwanted openings do not form beneath narrow portions of channel 381. Elastomer region 389 retracts into opening 383 of channel 381 when to open valve 380 when the pressure in channel 381 is reduced (e.g., to a vacuum) as discussed with respect to valves 340 and 360. The valves of FIGS. 15A-15J are discussed in further detail in PCT Patent Application Number PCT/US00/17740 mentioned above.

Layer 384 may be, for example, 1-1000 microns thick. Specific examples include 5, 10, 15, 20, 25, 35, 50, 60, 75, 85, 100, 150, 200, 250, 300, 350, 400, 450, 500, 550, 600, 650, 700, 750, 800, 850, 900, 950, and 1000 microns.

Channels 381-382 may be, for example, 0.1 micron-1 mm wide. Specific examples include 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, 100, 120, 140, 160, 180, 200, 250, 300, 350, 400, 450, 500, 550, 600, 650, 700, 750, 800, 850, 900, 950, and 1000 microns.

Microfluidic switches discussed in the present application may be coupled together to form multiplexers, using configurations known to those of skill in the semiconductor circuit art. Microfabricated fluidic switches, logic gates, and flip-flops discussed in the present application may be coupled together to perform mathematical functions such as addition, subtraction, multiplication, and division, using configurations known to those of skill in the semiconductor circuit art. Also, microfluidic devices of the present invention may be used to build devices that perform more complex functions. For example, the present invention includes microfluidic processors (CPU) that perform functions performed by electronic processors and are designed with the principles of the present invention and principles known in the circuit architecture art.

A further embodiment of the present invention includes structures and methods that provide high pressure sources for microfluidic applications. A high pressure source or a vacuum pressure source may be used as a power supply for microfluidic logic devices disclosed in this application. The pressure source is self-contained and self-recharging, making it ideal for devices that are implanted in the human body. The recharging mechanism works like a self-winding watch, in that motions in the device's environment are converted into potential energy.

Figure 16:
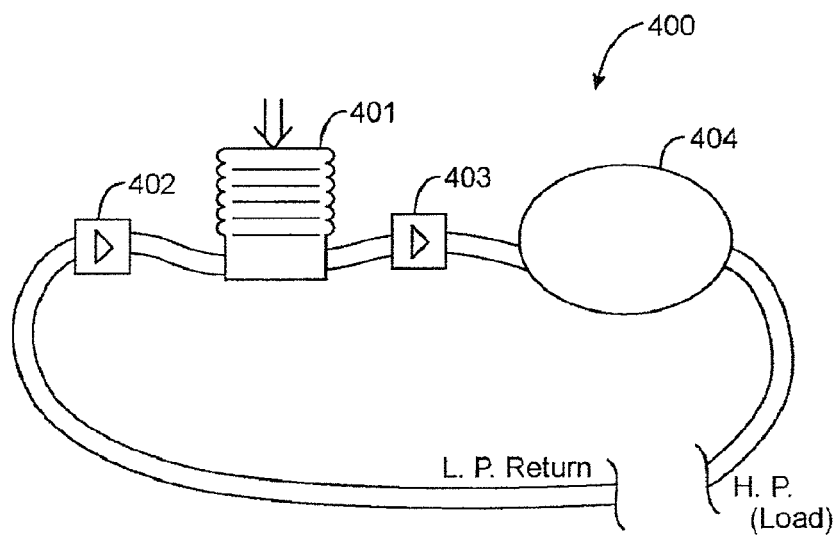
FIG. 16 shows a previously known macroscopic high pressure source.

Previously known macroscopic high pressure source 400 shown in FIG. 16 comprises four components: mechanical pump 401, a pair of unidirectional valves 402 and 403, and high pressure reservoir 404. Fluid is pulled from the low pressure L.P. return through unidirectional valve 402 into pump 401. Pump 401 then pumps fluid through unidirectional valve 403 into reservoir 404 which provides a high pressure source to a load at H.P. The working fluid in the system is recycled from the load, coupled to the high pressure H.P. outlet, back to the low pressure L.P. return.

Figure 17A:
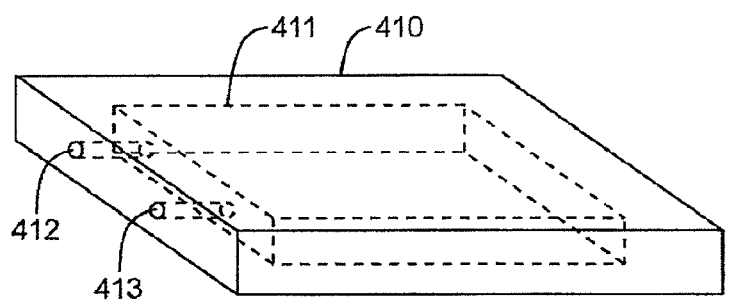
FIGS. 17A-17B show an example of a microfabricated fluidic pump.

A microfluidic pressure source may be constructed using microfabricated fluidic devices, as will now be discussed. An example of a microfabricated fluidic pump 410 comprised of elastic material is shown in FIG. 17A. Pump 410 has inner chamber 411, inlet conduit 412, and outlet conduit 413. Pump 410 may be integrated into a microfluidic chip, or may exist as a discrete component. The walls and the top and bottom surfaces of pump 410 may comprise elastomer material. If desired, the top and bottom surfaces of pump 410 (with respect to FIG. 17A) may comprise semi-rigid material.

Figure 17B:
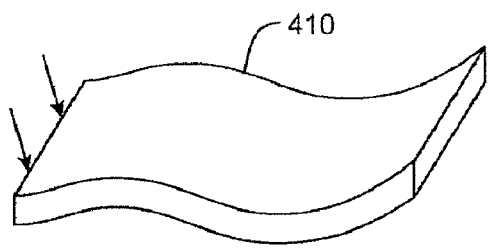

Pump 410 may be bent or compressed as shown in FIG. 17B to change the pressure within chamber 411 and to cause fluid to flow through conduits 412 and 413. When pump 410 is bent or compressed, the pressure of fluid in chamber 411 increases above the pressure in a fluid reservoir coupled outlet conduit 413, causing fluid to flow out of pump 410 through outlet conduit 413. When pump 410 is no longer bent or compressed, it returns to its normal position, and the pressure in chamber 411 decreases below the pressure in a fluid reservoir coupled to inlet conduit 412, causing fluid to flow into pump 410 through inlet conduit 412. In this way, pump 410 pumps fluid into and out of chamber 411. In microfluidic devices implanted in the human body, compression and bending occurs due to motion in the surrounding tissue causing pump 410 to perform its pumping action.

Pump 410 may be, for example, 100 microns to 10 cm wide. Specific examples include 100, 200, 300, 400, 500, 600, 700, 800, 900, 1000, 2000, 3000, 4000, 5000, 6000, 7000, 8000, and 9000 microns. Further examples are 1, 2, 3, 4, 5, 6, 7, 8, 9 and 10 cm.

Pump may be, for example, 5 microns to 10 mm thick. Specific examples include 5, 10, 20, 30, 40, 50, 60 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, and 10,000 microns.

Figure 18:
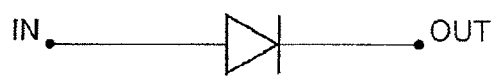
FIG. 18 shows the symbol for a unidirectional valve in microfluidics.
Figure 19:
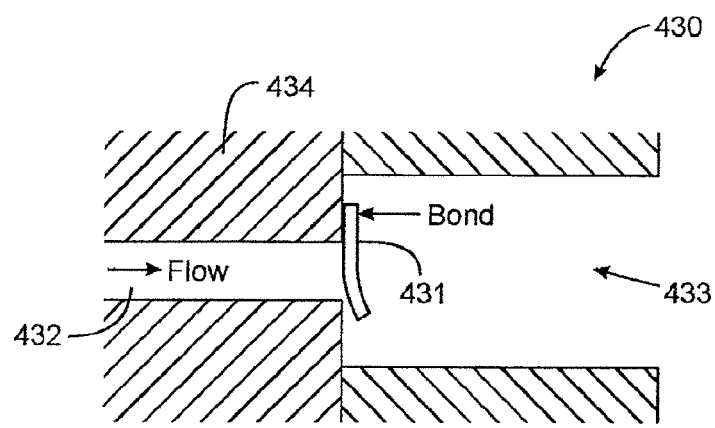
FIG. 19 shows a previously known macroscopic unidirectional valve.

The symbol for a unidirectional valve in microfluidics is shown in FIG. 18. Passive unidirectional valves may be constructed as macroscopic components by partially bonding a flap of RTV or similar elastic material over a feed through channel. Previously known macroscopic unidirectional valve 430 is shown in FIG. 19. Flap 431 of elastomer (which may comprise RTV) is bonded to the wall of layer 434 above feed through channel 432 as shown in FIG. 19. Fluid may flow through channel 432 into chamber 433 past flap 431. However, flap 431 prevents fluid from flowing from chamber 433 into channel 432, because it closes the opening of channel 432 when fluid flows in that direction. A similar scheme may be used to create a unidirectional valve like valve 430 on a microfluidic chip; however, high horizontal tolerances, or complex layering would be required.

Figure 20A:
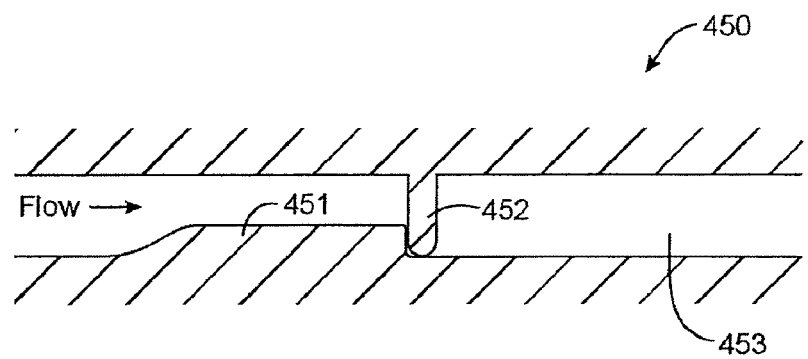
FIG. 20A is an embodiment of a unidirectional valve that can be made on a microfluidic chip.
Figure 20B:
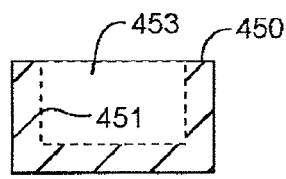
FIG. 20B shows a cross sectional view of channel 453.

The present invention provides more desirable designs for a microfluidic unidirectional valve. Unidirectional valve 450 in FIG. 20A is an embodiment of a unidirectional valve that can be made on a microfluidic chip. Valve 450 comprises a channel through elastomer material that has stopper 451 and elastomer flap 452 in channel 453. Valve 450 may comprise layers of elastomer material that are sealed together. Flap 452 is only attached to the top of channel 453. Flap 452 opens up to allow fluid to flow to the right in FIG. 20A through channel 453. Flap 452 and stopper 451 prevent fluid from flowing to the left in FIG. 20A through channel 453. When fluid begins to flow to the left, flap 452 presses up against stopper 451. Stopper 451 extends into channel 453 from the bottom and side walls of the channel as shown in the cross sectional view of FIG. 20B so that flap 452 forms a complete hermetic seal against stopper 451.

Channel 453 may be, for example, 5-1000 microns thick. Specific examples include 5, 10, 20, 30, 40, 50, 60 70, 80, 90, 100, 200, 300, 400, 500, 600, 700, 800, 900, and 1000 microns.

Flap 452 may be, for example, 5-1000 microns wide. Specific examples include 5, 10, 20, 30, 40, 50, 60 70, 80, 90, 100, 200, 300, 400, 500, 600, 700, 800, 900, and 1000 microns.

Flap 452 may be, for example, 1-200 microns thick. Specific examples include 1, 5, 10, 20, 30, 40, 50, 60 70, 80, 90, 100, 110, 120, 130, 140, 150, 160, 170, 180, 190, and 200 microns.

Stopper 451 may protrude, for example, 1-1000 microns into channel 453. Specific examples include 1, 5, 10, 20, 30, 40, 50, 60 70, 80, 90, 100, 200, 300, 400, 500, 600, 700, 800, 900, and 1000.

Figure 21:
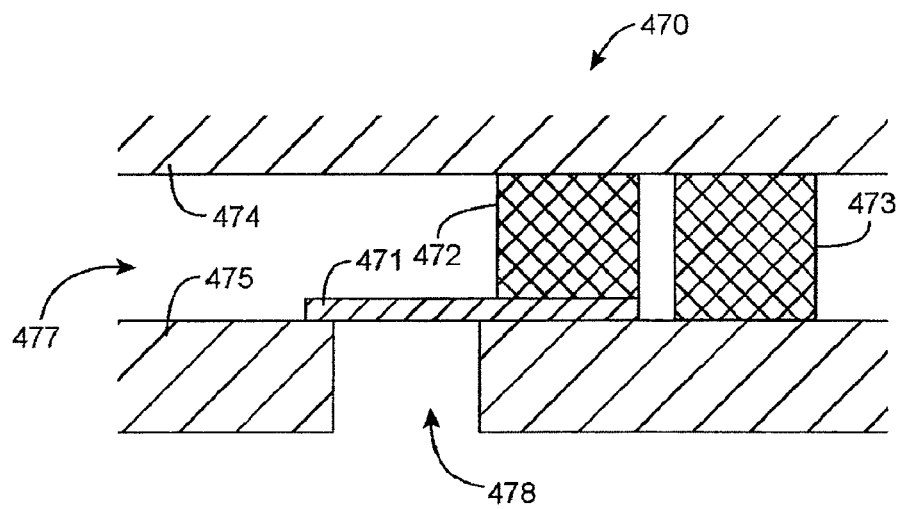
FIG. 21 is another embodiment of a microfluidic unidirectional value of the present invention that can be made on a microfluidic chip.

Unidirectional valve 470 shown in FIG. 21 is another embodiment of a microfluidic unidirectional value of the present invention that can be made on a microfluidic chip. Layers and regions 471-475 comprise an elastomer such as General Electric Silicones RTV (room temperature vulcanizing) 615, which comprises polydimethylsiloxane bearing vinyl groups and a platinum catalyst (hereinafter referred to as Part "A") and a cross-linker containing silicon hydride (Si—H) groups (hereinafter referred to as Part "B") which form a covalent bond with vinyl groups. RTV 615 is normally comprises of a ratio of 10:1 (Part A:Part B). For bonding, one layer of RTV 615 is made with a high Part A:Part B ratio (excess vinyl groups) such as a ratio of 30:1, and the other layer of RTV 615 is made with a low Part A:Part B ratio (excess Si—H groups) such as ratio of 3:1. An RTV 615 layer with a 30:1 ratio bonds to an RTV layer with a 3:1 ratio, but does not bond to another RTV layer with a 30:1 ratio. Also, an RTV 615 layer with a 3:1 ratio does not bond to another RTV layer with a 3:1 ratio.

Membrane 471, layer 474, and layer 475 all may comprise an elastomer such as RTV silicone with a low Part A to Part B ratio (e.g., 3:1). Spacer 472 and spacer 473 comprise an elastomer such as RTV silicone with a high Part A to Part B ratio (e.g., 30:1). Membrane 471 is held in place by spacer 472. Membrane 471 bonds to spacer 472, and spacer 472 bonds to layer 474. Spacer 473 bonds to layers 474 and 475. Membrane 471 does not bond to layer 475. Membrane 471 allows fluid to flow from feed-through 478 to channel 477, but prevents backflow of fluid from channel 477 to feed-through 478. Spacer 473 also blocks fluid flow in channel 477 to the right of feed through 478.

Channel 477 may be, for example, 0.1-5000 microns in width. Specific examples include 0.1, 0.3, 0.5, 0.7, 1, 2, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Membrane 471 may be, for example, 1-200 microns thick. Specific examples include 1, 5, 10, 20, 30, 40, 50, 60 70, 80, 90, 100, 110, 120, 130, 140, 150, 160, 170, 180, 190, and 200 microns.

Channel 478 may be, for example, 1-5000 microns in width. Specific examples include 1, 2, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns.

Figure 22:
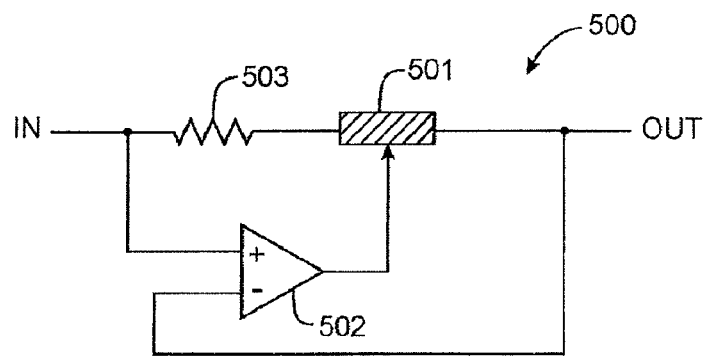
FIG. 22 shows another embodiment of a microfluidic unidirectional valve of the present invention.

Another embodiment of a microfluidic unidirectional valve of the present invention is shown in FIG. 22. Active "servo" unidirectional valve 500 shown in FIG. 22 advantageously does not require high horizontal tolerances. Unidirectional servo valve 500 is comprised of two devices: differential pressure multiplier 502 and pressure actuated normally closed switch 501. Switch 501 may be, for example, the embodiment of FIGS. 9A-9D. Resistor 503 represents the equivalent resistance for normally closed switch 501 in the "open" configuration.

Differential pressure multiplier 502 is the device described with respect to FIGS. 3 and 4A-4C. The $P_0$ chamber is connected to a second inlet source instead of ambient pressure (an embodiment discussed with respect to FIG. 4C), which is the pressure at output terminal OUT in valve 500. When the pressure at input terminal IN is less than the pressure at output terminal OUT, the pressure at the output of multiplier 502 and the gate of switch 501 is LOW so that switch 501 is closed. When the pressure at input terminal IN increases above the pressure at output terminal OUT, multiplier 502 increases the pressure at the gate of switch 501 above its threshold causing switch 501 to open so that fluid flows through switch 501 from IN to OUT.

Figure 23:
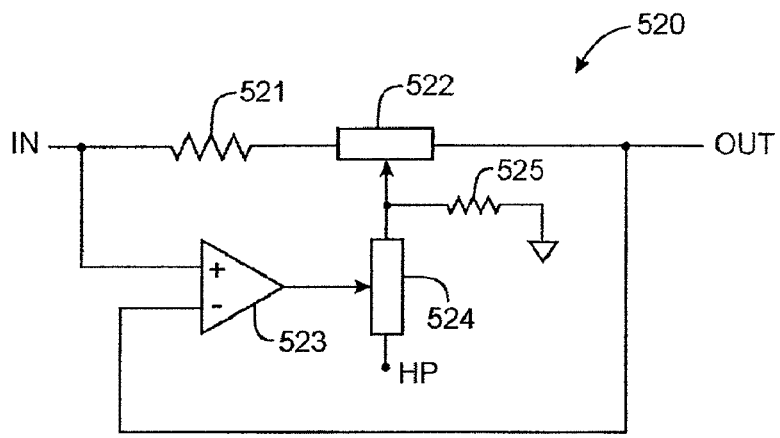
FIG. 23 shows a unidirectional active valve that may be constructed by using a pair of normally open switches.

In another embodiment of the present invention, a unidirectional active valve may be constructed by using a pair of normally open switches instead of the normally closed switch as shown in FIG. 23. Unidirectional valve 520 comprises differential pressure multiplier 523, pressure actuated normally open switches 522 and 524, and fluidic resistor 525. Resistor 521 represents the equivalent resistance for normally open switch 522 in the "open" configuration. When the pressure at input terminal IN is less than the pressure at output terminal OUT, multiplier 523 decreases the pressure at the gate of switch 524 below its threshold so that switch 524 is open. The pressure at the gate of switch 522 increases above its threshold, because it is coupled to high pressure terminal HP through switch 524, and the resistance of resistor 525 is much greater than the resistance of switch 524. Switch 522 closes and fluid cannot flow between IN and OUT.

When the pressure at IN is greater than the pressure at OUT, multiplier 523 increases the pressure at the gate of switch 524 above its threshold so that switch 524 is closed. The gate of switch 522 is now decoupled from high pressure terminal HP. The pressure at the gate of switch 522 decreases below the threshold of switch 522 through resistor 525, which is coupled to an ambient exhaust. Switch 522 opens and fluid can now flow between IN and OUT. Unidirectional valve 520, however, requires a high pressure source at terminal HP, and so valve 520 cannot be used to build the high pressure source itself. It could be used to recharge a high pressure reservoir if there is an independent means to charge the system initially.

Figure 24:
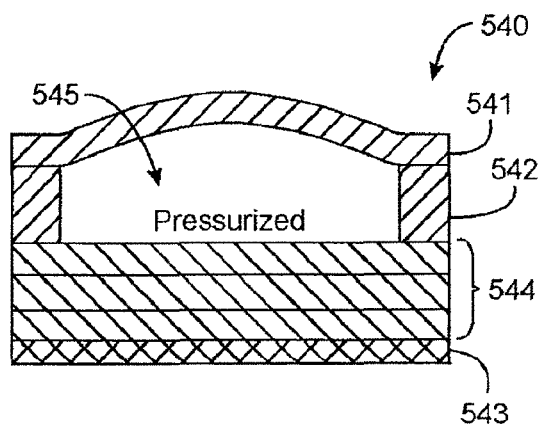
FIG. 24 shows an embodiment of a microfluidic high pressure reservoir that can be formed on a microfluidic chip.

An embodiment of a microfluidic high pressure reservoir that can be formed on a microfluidic chip is shown in FIG. 24. For an incompressible working fluid, the reservoir may be an elastic chamber similar to a water filled balloon, such as reservoir 540 shown in FIG. 24. Reservoir 540 includes elastomer layers 541-542 as well as elastomer layers 544 formed on rigid substrate 543. Devices that perform logic functions and other functionality may exist in layers 544. Elastomer layer 542 includes chamber 545 which may be pressurized through an inlet conduit (not shown). Elastomer layers 541, 542, and 544 are sealed together to form an elastomeric block.

As fluid is introduced into chamber 545 through the inlet conduit, the pressure in chamber 545 increases and elastomer layer 541 expands upwardly. When the pressure in chamber 545 decreases, layer 541 retracts downwardly. Chamber 545 also includes an outlet conduit (not shown) whereby high pressure fluid exits chamber 545. High pressure reservoir 540 is a capacitive element which has an appropriately small drop in pressure when a given amount of fluid is removed from chamber 545 to do work in a load device coupled to the outlet conduit.

Chamber 545 may be, for example, 5 microns to 10 mm wide. Specific examples include 5, 10, 20, 30, 40, 50, 60 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, and 10,000 microns.

Figure 25A:
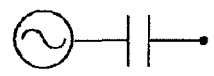
FIG. 25A shows the symbol for a microfluidic pump.
Figure 25B:
FIG. 25B shows the symbol for a microfluidic high pressure reservoir.

For a compressible working fluid such as air, the high pressure reservoir could be a rigid chamber of sufficient volume. The symbol for a microfluidic high pressure reservoir such as reservoir 540 is shown in FIG. 25B, which is the same symbol for a capacitor in the electronic arts. The symbol for a microfluidic pump is shown in FIG. 25A.

Figure 26:
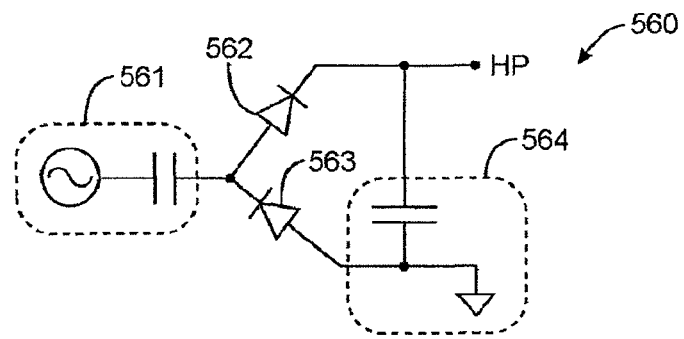
FIG. 26 shows a schematic for a microfabricated fluidic device that provides a high pressure source for microfluidic applications of the present invention.

A schematic for a microfabricated fluidic device that provides a high pressure source for microfluidic applications of the present invention is shown in FIG. 26. Device 560 includes microfluidic pump 561 coupled to microfluidic unidirectional valves 562 and 563, and microfluidic reservoir 564. Pump 561 may, for example, comprise pump 410 (FIGS. 17A-17B). Unidirectional valves 562-563 may, for example, comprise valves 450, 470, and 500 (FIGS. 20A-22). Reservoir 564 may, for example, comprise reservoir 540 (FIG. 24).

Fluid at ambient pressure is drawn through valve 563 into pump 561 when the pressure in pump 561 decreases. When the pressure in pump 561 increases, pump 561 then pumps fluid through valve 562 into reservoir 564. High pressure fluid may then be applied to load devices coupled to the HP terminal. Low pressure fluid is returned from the load devices to the ambient exhaust terminal. Fluid at ambient pressure returns to pump 561 through valve 563.

Figure 27:
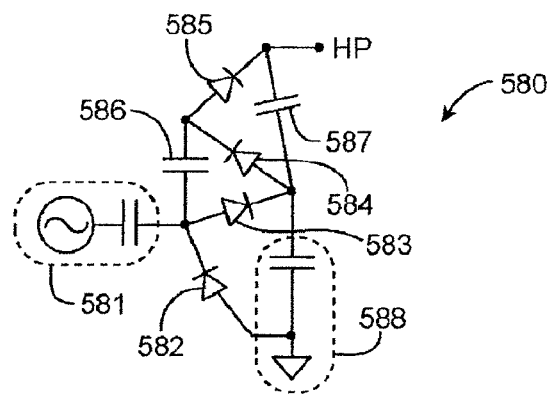
FIG. 27 shows a microfluidic generator.

Stages of microfluidic high pressure generators which multiply the output pressure may be coupled together to generate higher pressures as in a Cockroft-Walton generator. Microfluidic generator 580 shown in FIG. 27 includes microfluidic pump 581, microfluidic unidirectional valves 582-585, and microfluidic capacitors 586-588. An example of a microfluidic capacitor is shown and discussed with respect to FIG. 28 below. Pump 581 forces fluid through valve 583 and valve 585 via capacitor 586. The second stage which includes capacitor 586 and valves 584 and 585 doubles the output pressure at the HP terminal. Adding a third stage triples the pressure output; adding a fourth stage quadruples the pressure output, a fifth stage increases the pressure output by five times, a sixth stage increases the pressure output by six times, a seventh stage increases the pressure output by seven times, and so on.

Figure 28:
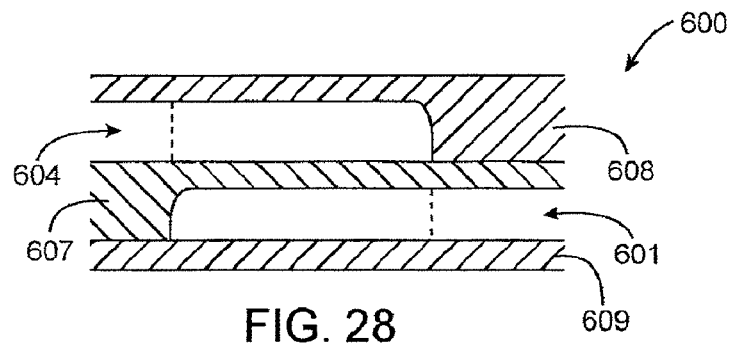
FIG. 28 shows a microfluidic capacitor that may be manufactured on a microfluidic chip.
Figure 29A:
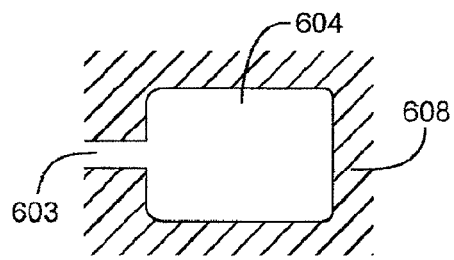
FIG. 29A shows a cross section view of layer 608.
Figure 29B:
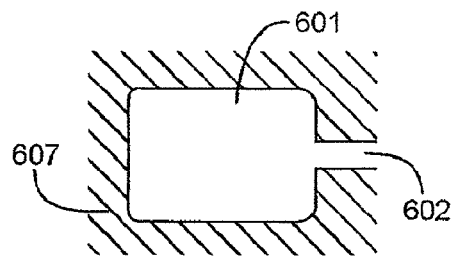
FIG. 29B shows a cross section view of layer 607.

In a further aspect of the present invention, a microfluidic capacitor that may be manufactured on a microfluidic chip is shown in cross section in FIG. 28. Capacitor 600 is formed of elastomer layers 607-608 that include chambers 601 and 604, respectively. A cross section view of layer 608 is shown in FIG. 29A, and a cross section view of layer 607 is shown in FIG. 29B. Fluid enters or exits chamber 604 through port 603, and fluid enters or exits chamber 601 through port 602. When the pressure of the fluid in chamber 604 increases above the pressure of the fluid in chamber 601, layer 607 flexes downwardly into chamber 601, causing the pressure in chamber 601 to rise. When the pressure of the fluid in chamber 601 increases above the pressure of the fluid in chamber 604, layer 607 flexes upwardly into chamber 604, causing the pressure in chamber 604 to rise.

Capacitor 600 allows fluid pressure to be transferred between two chambers that are not in fluid communication with each other. Fluidic capacitors are advantageous, because they allow pressure to be transferred between two fluids without requiring that the fluids mix with each other. Microfluidic capacitors also provide storage for high pressures and low pressures. Microfluidic capacitors also provide delays in pressure transfer which depend on the RC time constant associated with the microfluidic capacitor.

Chambers 604 and 601 may be, for example, 5 microns to 10 mm wide. Specific examples include 5, 10, 20, 30, 40, 50, 60 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, and 10,000 microns.

Figure 30:
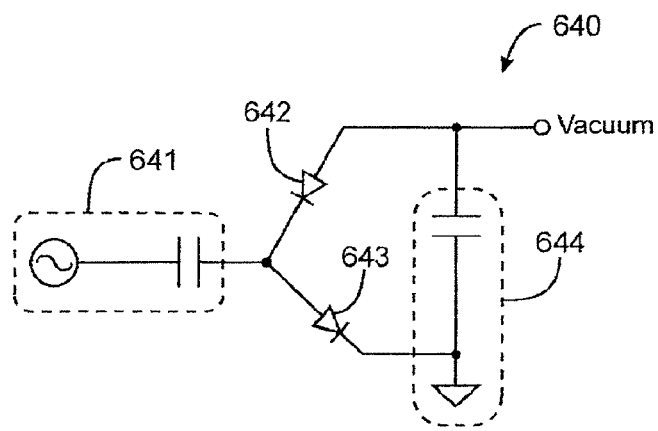
FIG. 30 shows the schematic for an embodiment of a vacuum pressure source.

The present invention also includes microfluidic vacuum pressure sources. The difference between ambient pressure and the vacuum generated by a microfluidic vacuum pressure source may be used to drive microfluidic devices on chip (instead of using a high pressure source). For example, a vacuum pressure source can drive vacuum actuated normally open and normally closed microfluidic switches. The schematic for an embodiment of a vacuum pressure source is shown in FIG. 30. Vacuum pressure source 640 includes pump 641, unidirectional valves 642-643, and vacuum reservoir 644. Vacuum pressure source 640 may maintain zero pressure or any other low pressure value in reservoir 644.

Fluid is drawn from vacuum reservoir 644 into pump 641 through unidirectional valve 642. Pump 641 then pumps fluid through valve 643 out through the ambient exhaust. Pump 641 maintains vacuum pressure or another low pressure value in reservoir 644 by removing fluid from it. Reservoir 644 is coupled to load devices at its vacuum terminal. Reservoir 644 acts as a vacuum source that is used to drive microfluidic load devices coupled to its vacuum terminal.

Figure 31:
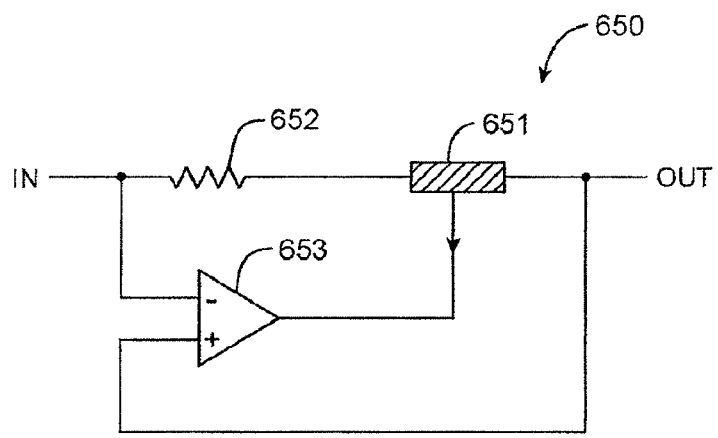
FIG. 31 shows a unidirectional valve.

Pump 641 may be, for example, microfluidic pump 410 in FIGS. 17A-17B. Examples of unidirectional valves 642 and 643 are shown in FIG. 31. Unidirectional valve 650 includes pressure microfluidic multiplier 653 and microfluidic vacuum actuated normally closed switch 651. Resistor 652 represents the equivalent resistance of switch 651 when it is open. Valve 650 allows fluid to flow from input terminal IN to output terminal OUT, but prevents fluid from flowing from OUT to IN. Multiplier 653 amplifies the difference between the pressure at OUT and the pressure at IN and applies it to the gate of switch 651. When the pressure at IN is less than the pressure at OUT, multiplier 653 increases the pressure at the gate of switch 651 above its threshold, causing switch 651 to be closed so that fluid cannot flow from OUT to IN. When the pressure at IN is greater than the pressure at OUT, multiplier 653 decreases the pressure at the gate of switch 651 below its threshold, causing switch 651 to be open so that fluid can flow from IN to OUT.

Figure 32:
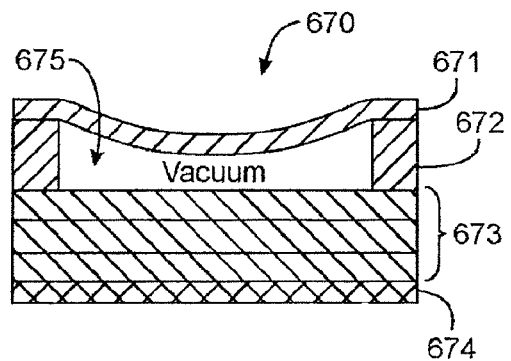
FIG. 32 shows an example of a microfluidic vacuum reservoir.

An example of microfluidic vacuum reservoir 644 is shown in FIG. 32. Vacuum reservoir 670 includes elastomer layers 671-672 as well as elastomer layers 673 which are formed on top of rigid substrate 674. Layers 673 may include microfluidic devices that perform logic functions and other functions. Layer 672 includes chamber 675 between layers 671 and 673. Chamber 672 may include inlet and output conduits (not shown).

When fluid is pumped out of chamber 675 (e.g., using pump 641) through the outlet conduit, elastomer layer 671 retracts downwardly as shown in FIG. 32, because the pressure in chamber 675 decreases. When fluid flows into chamber 675 from the load devices through the inlet conduit, layer 671 expands upwardly, because the pressure in chamber 675 increases. Vacuum reservoir 670 is a capacitive element which has an appropriately small drop in pressure when a given amount of fluid is added to chamber 675 to do work in a load device coupled to the outlet conduit.

Chamber 675 may be, for example, 5 microns to 10 mm wide. Specific examples include 5, 10, 20, 30, 40, 50, 60 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, and 10,000 microns.

Figure 33:
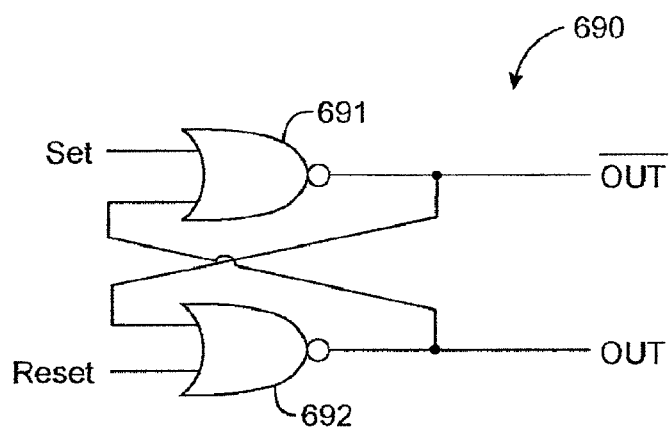
FIG. 33 is a flip-flop that includes cross-coupled microfluidic NOR gates.

A further embodiment of the present invention includes a microfluidic S-R flip-flip that is constructed from a pair of cross-coupled NOR gates. Flip-flop 690 in FIG. 33 includes cross-coupled microfluidic NOR gates 691 and 692. When the SET input of NOR gate 691 transitions from LOW to HIGH, the OUT signal goes HIGH and the $\overline{OUT}$ signal goes LOW. When the RESET input of NOR gate 692 transitions from LOW to HIGH, the OUT signal goes LOW and the $\overline{OUT}$ signal goes HIGH. When the SET input of NOR gate 691 and the RESET input of NOR gate 692 are both LOW, the OUT signal and the $\overline{OUT}$ signal both remain in their previous states. When the SET input of NOR gate 691 and the RESET input of NOR gate 692 are both HIGH, the OUT signal and the $\overline{OUT}$ signal are both LOW, which is an unstable state, because $\overline{OUT}$ and OUT cannot remain in that state when SET or RESET go LOW. The truth table for flip-flop 690 is shown below in Table 6.

TABLE 6

| SET | RESET | OUT | $\overline{OUT}$ |
|---|---|---|---|
| L to H to L | L | H | L |
| L | L to H to L | L | H |
| L | L | Previous State | Previous State |
| H | H | L | L |

Figure 34:
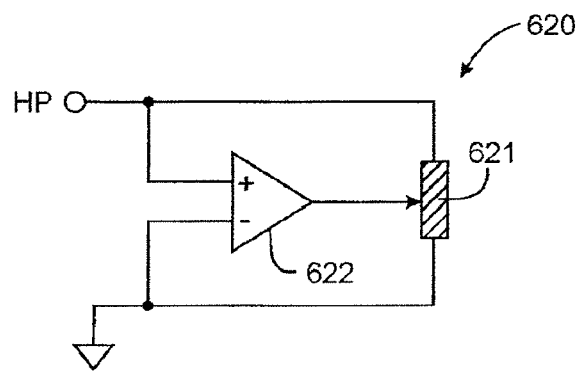
FIG. 34 shows a microfluidic switching regulator.

The microfluidic devices of the present invention also include devices that perform analog functions that are similar to the analog functions performed by analog circuits. For example, a microfluidic switching regulator is shown in FIG. 34. Regulator 620 is an embodiment of a microfluidic switching regulator of the present invention. Regulator 620 includes microfluidic pressure multiplier 622 and pressure actuated normally closed switch 621. The non-inverting input of multiplier 622 is coupled to a high pressure source (such as high pressure source 560), and the inverting input of multiplier 622 is coupled to ambient exhaust.

When the pressure at the high pressure HP terminal increases above ambient pressure, pressure multiplier 622 amplifies the difference between the pressure at the HP terminal and ambient pressure and applies it to the gate of switch 621. The gain of amplifier 622 is determined by equation (2) above as discussed with respect to FIG. 3. When the pressure at the HP terminal increases enough such that multiplier 622 increases the pressure at the gate of switch 621 above its threshold, switch 621 opens, causing fluid to flow from the HP terminal to ambient.

The pressure at the HP terminal now decreases. When the pressure at the HP terminal decreases enough such that multiplier 622 drops the pressure at the gate of switch 621 below its threshold, switch 621 closes, and the pressure at the HP terminal rises again. The geometry of differential pressure multiplier 622 is chosen to give it a gain such that it will open switch 621 at the desired pressure at the HP terminal. The gain of regulator 620 is chosen so that the pressure at the HP terminal is regulated to the desired value. Regulator 620 can be configured to regulate the pressure at the HP terminal to any desired value, by adjusting the gain of multiplier 622.

Figure 35A:
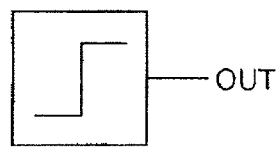
FIG. 35A shows a symbol for an pressure step source.
Figure 35B:
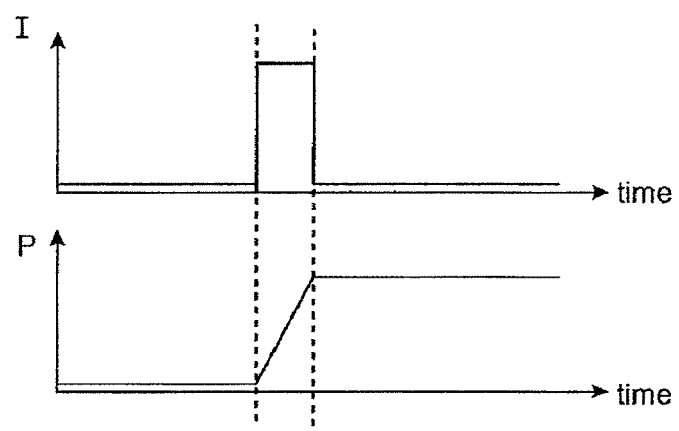
FIG. 35B shows a top graph of the current I through the sodium chloride solution in the channel and a bottom graph of the increase in pressure P at output terminal OUT.

A symbol for a pressure step source is shown in FIG. 35A. A pressure step source provides a rapidly increasing pressure signal at its output terminal OUT when a current signal is generated in the device. An example of a pressure step source is an electrolysis pressure source. The current signal is sent through sodium chloride solution in a channel within the electrolysis pressure source, that electrolyzes water in the solution to provide oxygen and hydrogen gas. The formation of gas bubbles in the sodium chloride solution causes the pressure in the channel to increase. The current I through the sodium chloride solution in the channel is shown in the top graph in FIG. 35B. The increase in pressure P at output terminal OUT is shown in the bottom graph of FIG. 35B.

The increasing pressure signal output by a step pressure source can rapidly open a normally closed valve or switch (or rapidly close a normally open valve or switch). However, the pressure in the channel of a pressure source (such as an electrolysis pressure source) does not decrease rapidly enough to re-open or re-close the valve or switch. The valve/switch remains closed for a lengthy period of time until the electrolytic gases have leaked away through the porous elastomer. Therefore, the pressure step source is not adequate by itself to rapidly open and close microfluidic valves and switches.

Figure 36A:
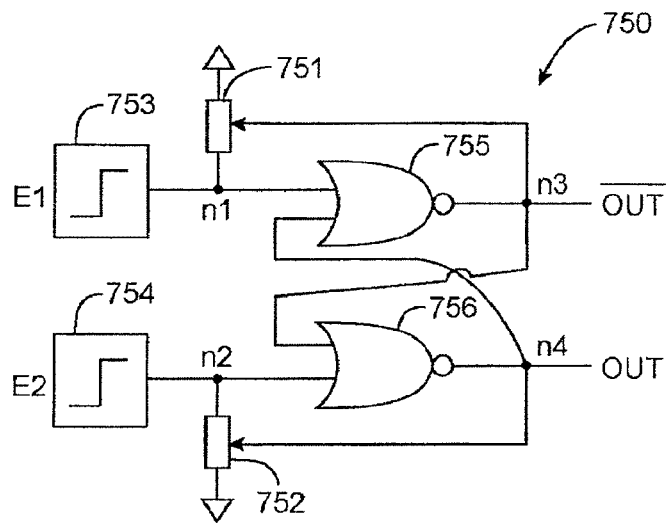
FIG. 36A shows a first embodiment of a microfluidic S-R flip-flop that is coupled to a pair of pressure step sources.

Structures and methods of the present invention provide ways to rapidly open and close valves and switches using a pair of pressure step sources, or by using a single step pressure source with appropriate delay logic. A first embodiment of a microfluidic S-R flip-flop that is coupled to a pair of pressure step sources is shown in FIG. 36A. Flip-flop 750 includes cross-coupled microfluidic NOR gates 755 and 756, pressure actuated normally open microfluidic switches 751 and 752, and pressure step sources 753-754.

Figure 36B:
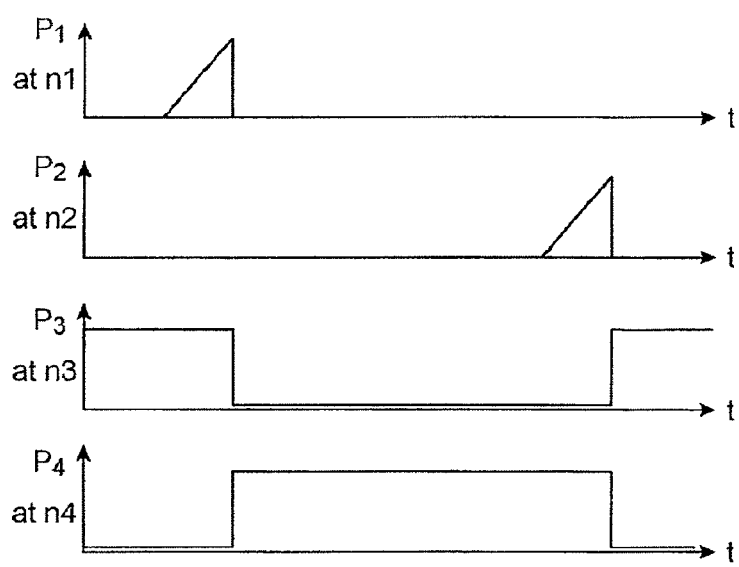
FIG. 36B shows pressure graphs for FIG. 36A.

When pressure source 753 causes the pressure $P_1$ at node n1 to increase above the threshold of NOR gate 755, NOR gate 755 causes pressure $P_3$ at node n3 at its output ($\overline{OUT}$) to go LOW, as shown by the graphs in FIG. 36B. When $P_3$ goes LOW, switch 751 opens, coupling node n1 to ambient exhaust. $P_1$ now goes LOW rapidly. There may be a propagation delay between the time $P_1$ goes HIGH and the time $P_3$ goes LOW, which is not shown in FIG. 36B. Also, when $P_3$ goes LOW, NOR gate 756 causes pressure $P_4$ at node n4 at its output (OUT) to go HIGH, closing switch 752. Flip-flop 750 latches the output signals at nodes n3 and n4 until the next pressure pulse at step pressure source 754.

When pressure source 754 causes pressure $P_2$ at node n2 to increase above the threshold of NOR gate 756, NOR gate 756 causes pressure $P_4$ at node n4 to go LOW as shown by the graphs in FIG. 36B. When $P_4$ goes LOW, switch 752 opens, coupling node n2 to ambient exhaust. The pressure $P_2$ at node n2 now rapidly goes LOW. There may be a propagation delay between the time $P_2$ goes HIGH and the time that $P_4$ goes LOW. When $P_4$ goes LOW, NOR gate 755 causes pressure $P_3$ at node n3 to go HIGH, closing switch 751 for the next cycle.

Flip-flop 750 latches the output signals at nodes n3 and n4 until the next pressure pulse at step pressure source 753. Flip-flop 750 can provide rapidly rising and falling HIGH and LOW signals at OUT and $\overline{OUT}$ at a high frequency, because it provides a system for bringing the pressure at the outputs of pressure sources 753-754 down rapidly. Flip-flip 750 uses two step pressure sources and six microfluidic normally-open pressure actuated switches to control one valve line coupled to outputs OUT and $\overline{OUT}$.

Figure 37A:
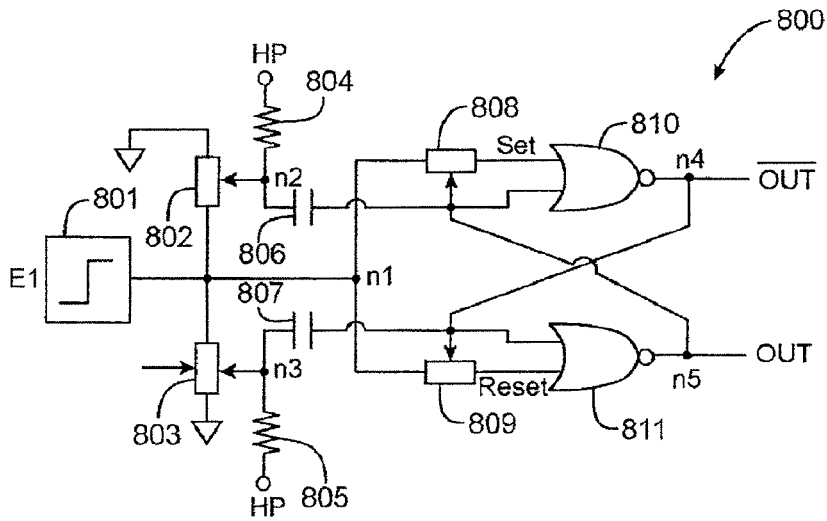
FIG. 37A shows a further embodiment of the present invention that provides a way to rapidly open and close a valve or a switch using a single step pressure source with appropriate delay logic.

A further embodiment of the present invention that provides a way to rapidly open and close a valve or a switch using a single step pressure source with appropriate delay logic is shown in FIG. 37A. Flip-flip 800 includes step pressure source 801, microfluidic pressure actuated normally open switches 802 and 803, microfluidic resistors 804 and 805, microfluidic capacitors 806 and 807, microfluidic pressure actuated normally open switches 808 and 809, and microfluidic NOR gates 810 and 811.

For purposes of the following illustrative discussion, it is assumed that pressure $P_4$ at node n4 (the output $\overline{OUT}$ of NOR gate 810) is at a HIGH level, and pressure $P_5$ at node n5 (the output OUT of NOR gate 811) is at a LOW level. Therefore, switch 808 is open, and switch 809 is closed. Pressure $P_3$ at node n3 is HIGH, because node n3 is coupled to a high pressure source HP through resistor 805. Pressure $P_2$ at node n2 is HIGH, because node n2 is coupled to a high pressure source HP through resistor 804.

Figure 37B:
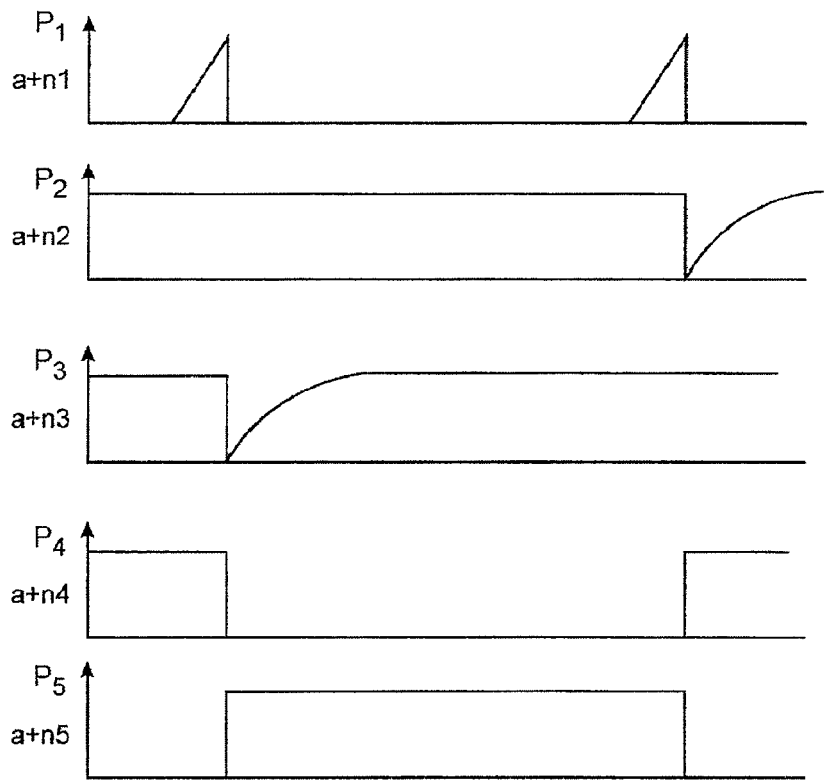
FIG. 37B shows pressure graphs for FIG. 37A.

When pressure source 801 causes pressure $P_1$ at node n1 to increase to a HIGH level, NOR gate 810 causes pressure $P_4$ at node n4 to go LOW, because switch 808 is open as shown in the graphs in FIG. 37B. When $P_4$ goes LOW, pressure $P_3$ at node n3 transitions LOW rapidly, because node n3 is coupled to node n4 through capacitor 807. Therefore, the decreasing pressure pulse at n4 is transferred to n3 as shown in FIG. 37B. When $P_3$ goes LOW, switch 803 opens and node n1 is vented to ambient pressure, causing pressure $P_1$ to go LOW. Subsequently pressure $P_3$ at node n3 increases back to a HIGH level according to the RC time constant of resistor 805 and capacitor 807. The RC time constant of resistor 805 and capacitor 807 is chosen to be long enough to fully vent pressure $P_1$ to ambient pressure when $P_4$ goes LOW.

Also, when $P_4$ goes LOW, NOR gate 811 causes pressure $P_5$ at node n5 to go HIGH. Switch 808 now closes, but $P_4$ remains LOW because $P_5$ (which is HIGH) is an input to NOR gate 810. Switch 809 opens, because $P_4$ is LOW. After $P_1$ goes LOW, $P_4$ and $P_5$ maintain their logic states.

After $P_3$ has returned to a HIGH state, pressure source 801 causes pressure $P_1$ at node n1 to increase to a HIGH level again. NOR gate 811 then causes pressure $P_5$ at node n5 to go LOW, because switch 809 is open as shown in the graphs in FIG. 37B. When $P_5$ goes LOW, pressure $P_2$ at node n2 transitions LOW rapidly, because node n2 is coupled to node n5 through capacitor 806. Therefore, the decreasing pressure pulse at n5 is transferred to n2 as shown in FIG. 37B. When $P_2$ goes LOW, switch 802 opens and node n1 is vented to ambient pressure, causing pressure $P_1$ to go LOW. Subsequently pressure $P_2$ at node n2 increases back to a HIGH level according to the RC time constant of resistor 804 and capacitor 806. The RC time constant of resistor 804 and capacitor 806 is chosen to be long enough to fully vent pressure $P_1$ to ambient pressure when $P_5$ goes LOW.

Also, when $P_5$ goes LOW, NOR gate 810 causes pressure $P_4$ at node n4 to go HIGH. Switch 809 now closes, but $P_5$ remains LOW because $P_4$ (which is HIGH) is an input to NOR gate 811. Switch 808 opens, because $P_5$ is LOW. After $P_1$ goes LOW, and $P_4$ and $P_5$ maintain their logic states. Switches 802 and 803 vent $P_1$ to ambient following each transition. Switches 808 and 809 toggle the output of pressure source 801 to the SET and RESET inputs of flip-flop 800.

Pulsing pressure $P_1$ toggles the output state of OUT and $\overline{OUT}$ between "on" and "off," providing signals that can rapidly open and close valves and switches. Flip-flop 800 can provide rapidly rising and falling HIGH and LOW signals at OUT and $\overline{OUT}$ at a high frequency, because it provides a system for bringing the pressure at the output of pressure source 801 down rapidly. Flip-flop 800 uses a single step pressure source and eight pressure actuated normally-open switches to control one valve line coupled to outputs OUT and $\overline{OUT}$.

Figure 38:
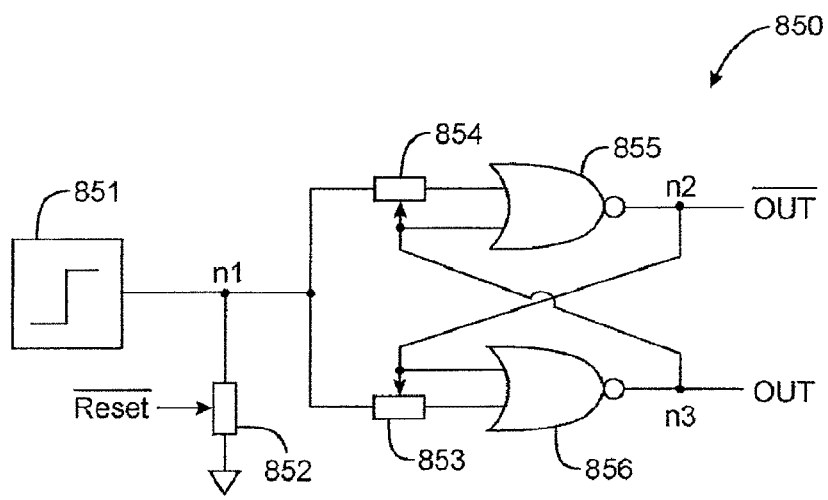
FIG. 38 shows a device for sections of the microfluidic logic which operate synchronously.

The devices of FIGS. 36A and 37A may be used in the general case of asynchronous logic. For sections of the microfluidic logic which operate synchronously, the device of FIG. 38 may be used. Flip-flop 850 includes step pressure source 851, microfluidic pressure actuated normally open switches 852-854, microfluidic NOR gates 855-856, and a single clock signal line ($\overline{RESET}$) coupled to the gate of switch 852. $\overline{RESET}$ is normally HIGH. All step sources including step pressure source 851 are vented simultaneously when $\overline{RESET}$ is LOW.

When pressure $P_1$ at node n1 goes HIGH, NOR gate 855 causes pressure $P_2$ at n2 to go LOW (assuming for illustration that switch 854 is open and switch 853 is closed). Subsequently, NOR gate 856 causes pressure $P_3$ at node n3 to go HIGH. Switch 854 now closes, and switch 853 opens. The pressures at $P_2$ and $P_3$ will hold their current states (LOW and HIGH, respectively), when $P_1$ goes LOW. When $\overline{RESET}$ subsequently goes LOW for short period of time, switch 852 opens, and $P_1$ is pulled LOW (to ambient pressure). $\overline{RESET}$ then returns to a HIGH state.

When $P_1$ subsequently goes HIGH again, NOR gate 856 causes pressure $P_3$ at n3 to go LOW (because switch 853 is open). Subsequently, NOR gate 855 causes pressure $P_2$ at node n2 to go HIGH. Switch 853 now closes, and switch 854 opens. The pressures at $P_2$ and $P_3$ hold their previous states (HIGH and LOW, respectively), until $P_1$ goes HIGH again. When $P_1$ goes HIGH again, the cycle repeats, and pressures at $P_2$ and $P_3$ change state again.

Figure 39A:
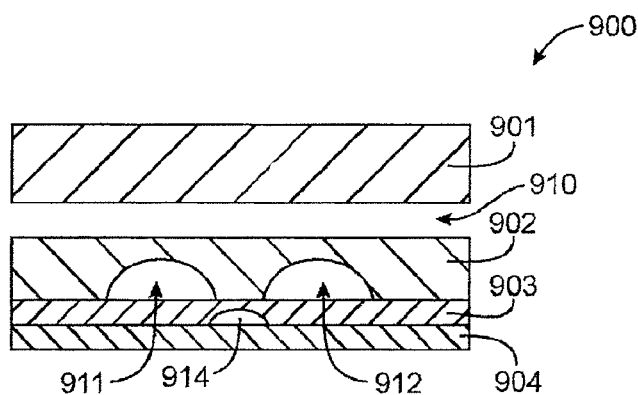
FIGS. 39A-39D show another microfluidic switch of the present invention.
Figure 39B:
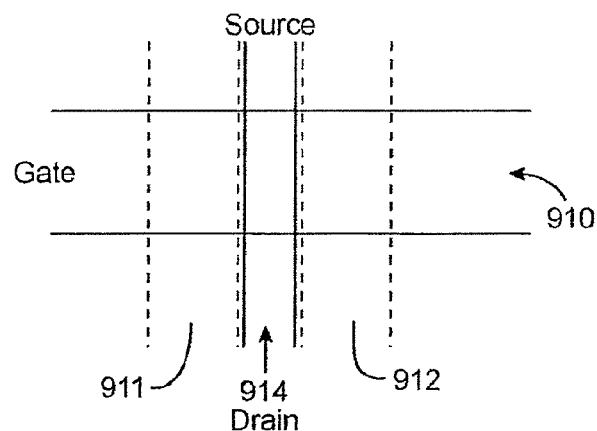
Figure 39C:
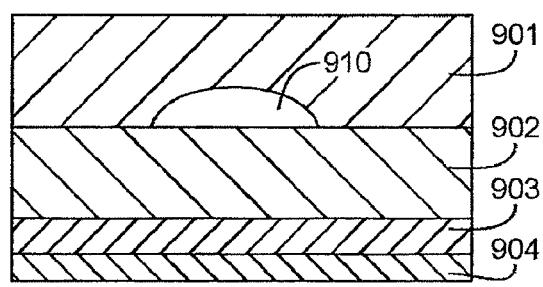

Another microfluidic switch of the present invention is shown in FIGS. 39A-39D. Pressure actuated normally open switch 900 includes elastomer layers 901, 902, and 903 that are form on top of rigid substrate 904. Layer 901 includes channel 910, which is the gate of the switch. Layer 902 includes chambers 911-912, which are shown by the dotted lines in the top down view of FIG. 39B. Chambers 911-912 are connected to ambient exhaust. Layer 903 includes channel 914, which couples the drain and the source of the switch. FIG. 39A is a cross section view along channel 910. FIG. 39C is a cross section view perpendicular to channel 910, that does not intersect chambers 911-912 or channel 914.

The pressure in chambers 911-912 may be at ambient pressure. When the pressure in gate channel 910 increases above ambient, the channel 910 presses down on the area between chambers 911-912. The V shaped cross-section of this elastomer layer concentrates force from a large area under channel 910 onto a small area over channel 910. When the pressure on channel 910 is increased enough, channel 914 closes, decoupling the source and the drain of switch 900.

Figure 39D:
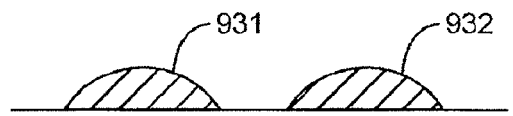

The pressure in channel 910 may be increased and decreased above and below a threshold to open and close channel 914 as a switch. Chambers 911-912 may be formed in layer 902 by placing photoresist on a silicon substrate, etching the photoresist, and then baking it to form photoresist regions 931 and 932 as shown in FIG. 39D. Elastomer is formed over regions 931-932, and regions 931-932 act as a mold to form chambers 911-912 in the elastomer layer.

Layer 901 may be, for example, 10 microns to 2 mm. Specific examples include 10, 20, 30, 40, 50, 60 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 11,000, 12,000, 13,000, 14,000, 15,000, 16,000, 17,000, 18,000, 19,000 and 20,000 microns.

Layers 902 and 903 may be, for example, 1-1000 microns. Specific examples include 1, 2, 3, 4, 5, 10, 20, 30, 40, 50, 60 70, 80, 90, 100, 200, 300, 400, 500, 600, 700, 800, 900, and 1000 microns.

Channel 910 and chambers 911-912 may be, for example, 2.5-5000 microns wide. Specific examples include 2.5, 5, 10, 15, 20, 25, 35, 50, 60, 75, 85, 100, 150, 200, 250, 300, 350, 400, 450, 500, 550, 600, 650, 700, 750, 800, 850, 900, 950, 1000, 1200, 1400, 1600, 2000, 2200, 2400, 2600, 2800, 3000, 3200, 3400, 3600, 3800, 4000, 4200, 4400, 4600, 4800, and 5000 microns. Channel 910 and chambers 911-912 may be, for example, 1-200 microns high.

Specific examples include 1, 5, 10, 20, 30, 40, 50, 60, 70, 80, 90, 100, 120, 140, 160, 180, and 200 microns.

Channel 914 may be, for example, 0.1-250 microns wide. Specific examples include 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, 100, 120, 140, 160, 180, 200, 210, 220, 225, and 250 microns.

Channel 910 and chambers 911-912 act as an inverted pyramid pressure structure that takes the force of a smaller pressure buildup in a larger area in channel 910, and concentrates that force into a larger pressure over a smaller area into channel 914 (where channel 914 intersects channel 910). Chambers 911-912 focus the pressure increase in channel 910 over channel 914. This design provides a way to amplify the effect of a pressure increase in channel 910 to open and close channel 914 without having to increase the pressure in channel 910 above the pressure in channel 914. Layer 901 may be referred to as the control layer, layer 902 is the focus layer, and layer 903 is the flow layer.

Chambers 911 and 912 allow channel 914 to be closed without having to increase the pressure in gate channel 910 above the pressure in drain-to-source channel 914. Therefore, switch 900 may be coupled with other microfluidic switches to perform logic functions and other functions, because switch 900 does not require a pressure drop from the gate channel to the source-to-drain channel.

Figure 40:
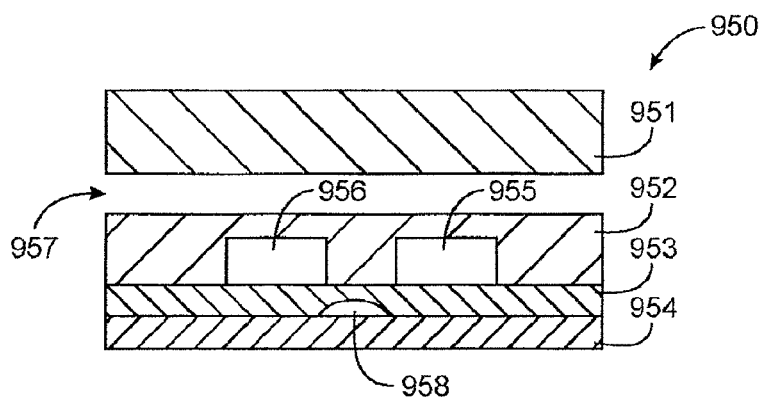
FIGS. 40-41 are other inverted pyramid pressure amplification switches.
Figure 41:
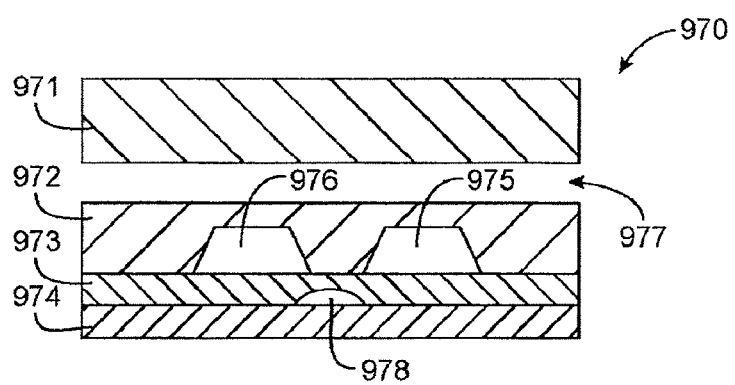

The present invention also includes other inverted pyramid pressure amplification switches, such as the switches 950 and 970 in FIGS. 40-41. Pressure actuated normally open switch 950 includes elastomer layers 951, 952, and 953 which are formed on rigid substrate 954. Layer 951 includes gate channel 957, layer 952 includes chambers 955-956, and layer 953 includes drain-to-source channel 958. Channel 957 is perpendicular to channel 958. When pressure in gate channel 957 increases, chambers 955-956 concentrate the force over channel 958 to close channel 958. Chambers 955-956 are rectangular, and therefore they provide less effective force transmission to channel 958 than chambers 911-912.

Pressure actuated normally open switch 970 includes elastomer layers 971, 972 and 973, which are formed on rigid substrate 974. Layer 971 includes gate channel 977, layer 972 includes chambers 975-976, and layer 973 includes drain-to-source channel 978. Channel 977 is perpendicular to channel 978. When pressure in gate channel 977 increases, chambers 975-976 concentrate the force over channel 978 to close channel 978. Chambers 975-976 concentrate the force from channel 977 over channel 978 more effectively than chambers 955-956, because chambers 975-976 are shaped as trapezoids.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the claims.

What is claimed is:

1. A microfabricated fluidic unidirectional valve comprising:
   a feed-through port bounded by a first elastomeric layer;
   a membrane fixed to the first elastomeric layer;
   a flow channel at least partly bounded by the first elastomeric layer, wherein the membrane selectively forms a seal with the first elastomeric layer to prevent fluid flow from the flow channel to the feed-through port and to allow fluid flow from the feed-through port through the flow channel;
   a second elastomeric layer bounding the flow channel; and
   a first spacer fixed to the second elastomeric layer and to the membrane, wherein the membrane is between the first spacer and the first elastomeric layer.

2. The microfabricated fluidic unidirectional valve of claim 1 wherein the membrane is attached to a side of the flow through channel.

3. The microfabricated fluidic unidirectional valve of claim 1 wherein the membrane deflects away from the first elastomeric layer in response to fluid pressure in the feed-through port being greater than fluid pressure in the flow channel.

4. The microfabricated fluidic unidirectional valve of claim 1 further comprising a second spacer between the first elastomeric layer and the second elastomeric layer.

5. The microfabricated fluidic unidirectional valve of claim 4, wherein the first spacer is between the membrane and the second elastomeric layer.

6. The microfabricated fluidic unidirectional valve of claim 5 wherein a fixed portion of the membrane is between the first spacer and the first elastomeric layer.

7. The microfabricated fluidic unidirectional valve of claim 5 wherein the second spacer is characterized by a thickness greater than a thickness of the first spacer.

8. The microfabricated fluidic unidirectional valve of claim 1 wherein the flow channel is characterized by a width between 0.1 μm and 1000 microns.

9. The microfabricated fluidic unidirectional valve of claim 1 wherein the membrane is characterized by a thickness between 1 μm and 200 μm.

10. The microfabricated fluidic unidirectional valve of claim 1 wherein the feed-through port is characterized by a width between 1 μm and 1000 μm.

* * * * *